United States Patent
Floyd et al.

(10) Patent No.: US 9,289,595 B2
(45) Date of Patent: Mar. 22, 2016

(54) MEDICAL LEAD TERMINATION SLEEVE FOR IMPLANTABLE MEDICAL DEVICES

(71) Applicant: CYBERONICS, INC., Houston, TX (US)

(72) Inventors: Jared Floyd, Ferndale, WA (US); Christopher Genau, Seattle, WA (US); Kent W. Leyde, Sammamish, WA (US)

(73) Assignee: CYBERONICS, INC., Houston, TX (US)

( * ) Notice: Subject to any disclaimer, the term of this patent is extended or adjusted under 35 U.S.C. 154(b) by 106 days.

(21) Appl. No.: 14/082,421

(22) Filed: Nov. 18, 2013

(65) Prior Publication Data

US 2014/0074212 A1    Mar. 13, 2014

Related U.S. Application Data

(63) Continuation of application No. 12/685,543, filed on Jan. 11, 2010, now Pat. No. 8,588,933.

(60) Provisional application No. 61/143,571, filed on Jan. 9, 2009.

(51) Int. Cl.
*A61N 1/05*    (2006.01)
*H01R 4/20*    (2006.01)
(Continued)

(52) U.S. Cl.
CPC .. *A61N 1/05* (2013.01); *H01R 4/20* (2013.01); *A61B 5/04* (2013.01); *A61B 5/4094* (2013.01); *H01R 2201/12* (2013.01); *Y10T 29/49218* (2015.01)

(58) Field of Classification Search
CPC ........ H01R 4/20; H01R 2201/12; A61N 1/05; A61B 5/04; Y10T 29/49218
See application file for complete search history.

(56) References Cited

U.S. PATENT DOCUMENTS 3,218,638 A    11/1965    Honig
3,498,287 A     3/1970    Ertl
(Continued)

FOREIGN PATENT DOCUMENTS

CA    2251852    4/1999
CA    2423840    2/2002
(Continued)

OTHER PUBLICATIONS

Adjouadi, et al. A new mathematical approach based on orthogonal operators for the detection of interictal spikes in epileptogenic data. Biomed. Sci. Instrum. 2004; 40: 175-80.

(Continued)

*Primary Examiner* — Catherine Voorhees

(57) ABSTRACT

A wire and electrode combination suitable for use with implanted medical devices, and a method for coupling the wire and electrode to achieve a robust electrical connection suitable for use with such medical devices are disclosed. The apparatus employs a wire that is optimized for strength, an electrode optimized for biocompatibility, and a termination sleeve with a closed distal end for coupling the wire to the electrode, while eliminating the potential for galvanic corrosion, enhancing weld quality, and facilitating manufacture of the apparatus. The method involves compressing the sleeve to engage the wire at two locations, where contact between the sleeve and wire at the first location seals the interior of the sleeve, and contact between the sleeve and wire at the second location electrically couples the wire to the sleeve. The sleeve, which is easier to manipulate than the wire, is then spot welded to the electrode.

21 Claims, 9 Drawing Sheets

(51) Int. Cl.
*A61B 5/04* (2006.01)
*A61B 5/00* (2006.01)

(56) References Cited

U.S. PATENT DOCUMENTS

| | | |
|---|---|---|
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strob et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkam |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,934,372 A | 6/1990 | Corenman et al. |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 5,010,891 A | 4/1991 | Chamoun |
| 5,016,635 A | 5/1991 | Graupe |
| 5,025,807 A | 6/1991 | Zabara |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deCoriolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun et al. |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,517,115 A | 5/1996 | Prammer |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |

(56) References Cited

U.S. PATENT DOCUMENTS

| | | |
|---|---|---|
| 5,782,798 A | 7/1998 | Rise |
| 5,782,874 A | 7/1998 | Loos |
| 5,792,186 A | 8/1998 | Rise |
| 5,800,474 A | 9/1998 | Benabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,869,804 A * | 2/1999 | Mueller et al. ............ 219/121.64 |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |
| 5,931,791 A | 8/1999 | Saltzstein et al. |
| 5,938,689 A | 8/1999 | Fischell et al. |
| 5,941,906 A | 8/1999 | Barreras et al. |
| 5,950,632 A | 9/1999 | Reber et al. |
| 5,957,861 A | 9/1999 | Combs et al. |
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,163 A | 5/2000 | John |
| 6,081,744 A | 6/2000 | Loos |
| 6,094,598 A | 7/2000 | Elsberry et al. |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,208,893 B1 | 3/2001 | Hofmann |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,795 B1 | 4/2002 | Bremer et al. |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,854 B1 | 6/2002 | Tziviskos et al. |
| 6,427,086 B1 | 7/2002 | Fischell et al. |
| 6,434,419 B1 | 8/2002 | Gevins et al. |
| 6,442,421 B1 | 8/2002 | Le Van Quyen et al. |
| 6,443,891 B1 | 9/2002 | Grevious |
| 6,453,198 B1 | 9/2002 | Torgerson |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,505,077 B1 | 1/2003 | Kast et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 | 4/2003 | Osorio et al. |
| 6,553,262 B1 | 4/2003 | Lang et al. |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,597,954 B1 | 7/2003 | Fischell et al. |
| 6,600,956 B2 | 7/2003 | Maschino |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,658,287 B1 | 12/2003 | Litt et al. |
| 6,665,562 B2 | 12/2003 | Gluckman et al. |
| 6,668,191 B1 | 12/2003 | Boveja |
| 6,671,553 B1 * | 12/2003 | Doan et al. ...................... 607/37 |
| 6,671,555 B2 | 12/2003 | Gielen |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,819,956 B2 | 11/2004 | DiLorenzo |
| 6,879,859 B1 | 4/2005 | Boveja |
| 6,893,395 B1 | 5/2005 | Kraus et al. |
| 6,901,294 B1 | 5/2005 | Whitehurst et al. |
| 6,901,296 B1 | 5/2005 | Whitehurst et al. |
| 6,912,419 B2 | 6/2005 | Hill |
| 6,921,538 B2 | 7/2005 | Donovan |
| 6,921,541 B2 | 7/2005 | Chasin et al. |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |
| 6,944,501 B1 | 9/2005 | Pless |
| 6,950,706 B2 | 9/2005 | Rodriquez |
| 6,973,342 B1 | 12/2005 | Swanson |
| 6,990,372 B2 | 1/2006 | Perron et al. |
| 7,010,351 B2 | 3/2006 | Firlik et al. |
| 7,089,059 B1 | 8/2006 | Pless |
| 7,174,212 B1 | 2/2007 | Klehn et al. |
| 7,177,701 B1 | 2/2007 | Pianca |
| 7,209,787 B2 | 4/2007 | DiLorenzo |
| 7,212,851 B2 | 5/2007 | Donoghue et al. |

(56) References Cited

U.S. PATENT DOCUMENTS

| | | |
|---|---|---|
| 7,231,254 B2 | 6/2007 | DiLorenzo |
| 7,242,984 B2 | 7/2007 | DiLorenzo |
| 7,277,758 B2 | 10/2007 | DiLorenzo |
| 7,324,851 B1 | 1/2008 | DiLorenzo |
| 7,373,198 B2 | 5/2008 | Bibian et al. |
| 7,403,820 B2 | 7/2008 | DiLorenzo |
| 7,463,917 B2 | 12/2008 | Martinez |
| 7,623,928 B2 | 11/2009 | Dilorenzo |
| 7,631,015 B2 | 12/2009 | Gupta et al. |
| 7,747,325 B2 | 6/2010 | DiLorenzo |
| 7,805,196 B2 | 9/2010 | Miesel et al. |
| 7,853,329 B2 | 12/2010 | DiLorenzo |
| 7,881,798 B2 | 2/2011 | Miesel et al. |
| 8,036,736 B2 | 10/2011 | Snyder et al. |
| 8,055,348 B2 | 11/2011 | Heruth et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1 | 8/2002 | Echauz et al. |
| 2002/0109621 A1 | 8/2002 | Khair et al. |
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Pless et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2003/0204228 A1 | 10/2003 | Cross, Jr. et al. |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010113 A1 | 1/2005 | Hall et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021105 A1 | 1/2005 | Firlik et al. |
| 2005/0021108 A1 | 1/2005 | Klosterman et al. |
| 2005/0021313 A1 | 1/2005 | Nititin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad |
| 2005/0197590 A1 | 9/2005 | Osorio et al. |
| 2005/0203366 A1 | 9/2005 | Donoghue et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0074450 A1* | 4/2006 | Bartels et al. .................. 607/119 |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |

(56) References Cited

U.S. PATENT DOCUMENTS

| | | |
|---|---|---|
| 2006/0224191 A1 | 10/2006 | Dilorenzo |
| 2006/0253096 A1 | 11/2006 | Blakley et al. |
| 2006/0293578 A1 | 12/2006 | Rennaker, II |
| 2006/0293720 A1 | 12/2006 | DiLorenzo et al. |
| 2007/0027367 A1 | 2/2007 | Oliver et al. |
| 2007/0027514 A1 | 2/2007 | Gerber |
| 2007/0035910 A1 | 2/2007 | Stevenson |
| 2007/0043459 A1 | 2/2007 | Abbott, II et al. |
| 2007/0055320 A1 | 3/2007 | Weinand |
| 2007/0060973 A1 | 3/2007 | Ludvig et al. |
| 2007/0073355 A1 | 3/2007 | DiLorenzo |
| 2007/0073357 A1 | 3/2007 | Rooney et al. |
| 2007/0100398 A1 | 5/2007 | Sloan |
| 2007/0149952 A1 | 6/2007 | Bland et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0167991 A1 | 7/2007 | DiLorenzo |
| 2007/0185890 A1 | 8/2007 | VanEpps et al. |
| 2007/0213629 A1 | 9/2007 | Greene |
| 2007/0213785 A1 | 9/2007 | Osorio et al. |
| 2007/0217121 A1 | 9/2007 | Fu et al. |
| 2007/0238939 A1 | 10/2007 | Giftakis et al. |
| 2007/0244407 A1 | 10/2007 | Osorio |
| 2007/0250077 A1 | 10/2007 | Skakoon et al. |
| 2007/0250901 A1 | 10/2007 | McIntire et al. |
| 2007/0287931 A1 | 12/2007 | DiLorenzo |
| 2008/0021341 A1 | 1/2008 | Harris et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0082019 A1 | 4/2008 | Ludving et al. |
| 2008/0091090 A1 | 4/2008 | Guillory et al. |
| 2008/0103556 A1 | 5/2008 | Li et al. |
| 2008/0114417 A1 | 5/2008 | Leyde |
| 2008/0119900 A1 | 5/2008 | DiLorenzo |
| 2008/0161712 A1 | 7/2008 | Leyde |
| 2008/0161713 A1 | 7/2008 | Leyde et al. |
| 2008/0183096 A1 | 7/2008 | Snyder et al. |
| 2008/0183097 A1 | 7/2008 | Leyde et al. |
| 2008/0208074 A1 | 8/2008 | Snyder et al. |
| 2008/0221876 A1 | 9/2008 | Holdrich |
| 2008/0255582 A1 | 10/2008 | Harris |
| 2008/0273287 A1 | 11/2008 | Marinkov et al. |
| 2008/0319281 A1 | 12/2008 | Aarts |
| 2009/0018609 A1 | 1/2009 | DiLorenzo |
| 2009/0062682 A1 | 3/2009 | Bland et al. |
| 2009/0062696 A1 | 3/2009 | Nathan et al. |
| 2009/0117787 A1* | 5/2009 | Kerner ......................... 439/877 |
| 2009/0171168 A1 | 7/2009 | Leyde et al. |
| 2009/0171420 A1 | 7/2009 | Brown et al. |
| 2009/0264952 A1 | 10/2009 | Jassemidis et al. |
| 2010/0023089 A1 | 1/2010 | DiLorenzo |
| 2010/0125219 A1 | 5/2010 | Harris et al. |
| 2010/0145176 A1 | 6/2010 | Himes |
| 2010/0168603 A1 | 7/2010 | Himes et al. |
| 2010/0168604 A1 | 7/2010 | Echauz et al. |
| 2010/0217348 A1 | 8/2010 | DiLorenzo |
| 2010/0302270 A1 | 12/2010 | Echauz et al. |
| 2011/0166430 A1 | 7/2011 | Harris et al. |
| 2011/0172554 A1 | 7/2011 | Leyde et al. |
| 2011/0201944 A1 | 8/2011 | Higgins et al. |
| 2011/0213222 A1 | 9/2011 | Leyde et al. |
| 2011/0218820 A1 | 9/2011 | Himes et al. |
| 2011/0219325 A1 | 9/2011 | Himes et al. |
| 2011/0260855 A1 | 10/2011 | John et al. |
| 2011/0319785 A1 | 12/2011 | Snyder et al. |

FOREIGN PATENT DOCUMENTS

| | | |
|---|---|---|
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022D | 12/2005 |
| EP | 0124663 | 11/1984 |
| EP | 0898460 | 3/1999 |
| EP | 1145735 | 10/2001 |
| EP | 1145736 | 10/2001 |
| EP | 1307260 | 5/2003 |
| EP | 1335668 | 8/2003 |
| EP | 1525551 | 4/2005 |
| EP | 0911061 | 10/2005 |
| EP | 1609414 | 12/2005 |
| JP | 24033673 | 2/2004 |
| SU | 1074484 | 2/1984 |
| WO | 8501213 | 3/1985 |
| WO | 9200119 | 1/1992 |
| WO | 9726823 | 7/1997 |
| WO | 9734522 | 9/1997 |
| WO | 9734524 | 9/1997 |
| WO | 9734525 | 9/1997 |
| WO | 9739797 | 10/1997 |
| WO | 9742990 | 11/1997 |
| WO | 9745160 | 12/1997 |
| WO | 9849935 | 11/1998 |
| WO | 9920342 | 4/1999 |
| WO | 9956821 | 11/1999 |
| WO | 9956822 | 11/1999 |
| WO | 0007494 | 2/2000 |
| WO | 0010455 | 3/2000 |
| WO | 0141867 | 6/2001 |
| WO | 0148676 | 7/2001 |
| WO | 0149364 | 7/2001 |
| WO | 0167288 | 9/2001 |
| WO | 0175660 | 10/2001 |
| WO | 0209610 | 2/2002 |
| WO | 0209811 | 2/2002 |
| WO | 0236003 | 5/2002 |
| WO | 0238031 | 5/2002 |
| WO | 0238217 | 5/2002 |
| WO | 0249500 | 6/2002 |
| WO | 02058536 | 8/2002 |
| WO | 02067122 | 8/2002 |
| WO | 03001996 | 1/2003 |
| WO | 03009207 | 1/2003 |
| WO | 03030734 | 4/2003 |
| WO | 03035165 | 5/2003 |
| WO | 03084605 | 10/2003 |
| WO | 2004008373 | 1/2004 |
| WO | 2004032720 | 4/2004 |
| WO | 2004034231 | 4/2004 |
| WO | 2004034879 | 4/2004 |
| WO | 2004034880 | 4/2004 |
| WO | 2004034881 | 4/2004 |
| WO | 2004034882 | 4/2004 |
| WO | 2004034883 | 4/2004 |
| WO | 2004034885 | 4/2004 |
| WO | 2004034982 | 4/2004 |
| WO | 2004034997 | 4/2004 |
| WO | 2004034998 | 4/2004 |
| WO | 2004035130 | 4/2004 |
| WO | 2004036370 | 4/2004 |
| WO | 2004036372 | 4/2004 |
| WO | 2004036376 | 4/2004 |
| WO | 2004036377 | 4/2004 |
| WO | 2004037342 | 5/2004 |
| WO | 2004043536 | 5/2004 |
| WO | 2004091718 | 10/2004 |
| WO | 2005007236 | 1/2005 |
| WO | 2005028026 | 3/2005 |
| WO | 2005028028 | 3/2005 |
| WO | 2005031630 | 4/2005 |
| WO | 2005051167 | 6/2005 |
| WO | 2005051306 A2 | 6/2005 |
| WO | 2005117693 | 12/2005 |
| WO | 2006014971 | 2/2006 |
| WO | 2006014972 | 2/2006 |

(56) References Cited

FOREIGN PATENT DOCUMENTS

WO      2006020794      2/2006
WO      2006035392      4/2006

OTHER PUBLICATIONS

Adjouadi, et al. Detection of interictal spikes and artifactual data through orthogonal transformations. J. Clin. Neuorophysiol. 2005; 22(1):53-64.

Adjouadi, et al. Interictal spike detection using the Walsh transform. IEEE Trans. Biomed. Eng. 2004; 51(5):868-72.

Aksenova, et al. On-line disharmony detection for early prediction of epilepsy seizure onset. 5th International Workshop Neural Coding 2003. Aulla (Italy) Sep. 20-25, 2003. (Abstract).

Aksevnova, et al. Nonparametric on-line detection of changes in signal spectral characteristics for early prediction of epilepsy seizure onset. J. Automation and Information Sciences. 2004; 36(8): 35-45.

Andrzejak, et al. Testing the null hypothesis of the nonexistence of a preseizure state. Physical Review E. 2003; 67: 010901-1-010901-4.

Andrzejak, et al. Bivariate surrogate techniques: necessity, strengths, and caveats. Physical Review E. 2003; 68: 066202-1-066202-15.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. J Mol. Biol. 13: 238-252.

Baruchi, et al. Functional holography of complex networks activity—From cultures to the human brain. Complexity. 2005; 10(3): 38 R 51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modeling, Indentification, and Control. 2003; 377-201: 313-317.

Bhattacharya, et al. Enhanced phase synchrony in the electroencephalograph gamma band for musicians while listing to music. Phys. Rev. E. 2001; 64:012902-1-4.

Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. PHYSICA D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporary lobe epilepsy. Electroencephalogr. Clin Neurophysiol. 1997; 102(2): 98-105.

Cerf, et al. Critically and synchrony of fluctuations in rhythmical brain activity: pretransitional effects in epileptic patients. Biol. Cybern. 2004; 90(4): 239-55.

Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al Spatio-temporal dynamics prior to neocortical seizures: amplitude versphase couplings. IEEE Trans. Biomed. Eng. 2003; 50(5):571-83.

Chen et al.; Clinical utility of video-EEG monitoring; Perdiatric Neurology; vol. 12; No. 3; pp. 220-224; 1995.

Crichton, Michael, "Terminal Man", 1972, Ballantine Books, NY, NY, pp. 21-24, 32-33, 70-71, and 74-81.

D'Alessandro, et al. A multi-feature and multi-channel univariate selection process for seizure prediction. Clin. Neurophysiol. 2005; 116(3): 506-16.

D'Alessandro, et al. Epileptic seizure prediction using hybrid feature selection over multiple intracranial EEG electrode contacts: a report of four patients. IEEE Trans. Biomed. Eng. 2003; 50(5): 603-15.

DiLorenzo, Daniel, U.S. Appl. No. 11/282,317 entitled "Closed-loop vag nerve stimulation," filed Nov. 17, 2005.

Drury, et al. Seizure prediction using scalp electroencephalogram. Exp. Neurol. 2003; 184 Suppl 1: S9-18.

Ebersole, J.S. In search of seizure prediction: a critique. Clin. Neurophysiol. 2005; 116(3); 489-92.

Ebersole, J.S. Functional neuroimaging with EEG source models to localize epileptogenic foci noninvasively. Neurology. Available at http://www.uchospitals.edu/pd/uch_0014471.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagnerve stimulation for epilepsy, A report of the therapeutics and technology assessment subcommittee of the American Academy of Neurology. Neurology.53: 666-669.

Franaszczuk et al.; An autoregressive method for the measurement of synchronization of interictal and ictal EEG signals; Biological Cybernetics, vol. 81; No. 1; pp. 3-9; 1999.

Gardner, A. B. A Novelty Detection Approach to Seizure Analysis from Intracranial EEG. Georgia Institute of Technology. Apr. 2004. A dissertation available at http://etd.gatech.edu/theses/available/etd-04122004-132404/unrestricted/gardner_andrew_b_200405.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

(56) References Cited

OTHER PUBLICATIONS

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.
Harrison, et al. Accumulated energy revised. Clin. Neurophysiol. 2005; 116(3):527-31.
Harrison, et al. Correlation dimension and integral do not predict epileptic seizures. Chaos. 2005; 15(3): 33106-1-15.
Hearst M. Trends & Controversies: Support Vector Machines. IEEE Intelligent Systems. 1998; 13: 18-28.
Hively, et al. Channel-consistent forewarning of epileptic events from scalp EEG. IEEE Trans. Biomed. Eng. 2003; 50(5): 584-93.
Hively, et al. Detecting dynamical changes in nonlinear time series. Physics Letters A. 1999; 258: 103-114.
Hively, et al. Epileptic Seizure Forewarning by Nonlinear Techniques. ORNL/TM-2000/333 Oak Ridge National Laboratory. Nov. 2000. Available at http://computing.ornl.gov/cse_home/staff/hively/NBICradaAnnualRpt_FY00.pdf. Accessed Feb. 28, 2006.
Hjorth, B. Source derivation simplifies topographical EEG interpretation. Am. J. EEG Technol. 1980; 20:121-132.
Hsu, et al. A practical guide to support vector classification. Technical report, Department of Computer Science and information Technology, National Taiwan University, 2003. Available at http://www.csie.ntu.edu.tw/~cjin/papers/guide/guide.pdf. Accessed Feb. 28, 2006.
Huynh, J. A. Evaluation of Gene Selection Using Support Vector Machine Recursive Feature Elimination. Presentation slides. (41 pages) (May 26, 2004).
Huynh, J. A. Evaluation of Gene Selection Using Support Vector Machine Recursive Feature Elimination. Arizona State University. May 26, 2004. (28 pages).
Iasemidis, et al. Adaptive epileptic seizure prediction system. IEEE Trans. Biomed. Eng. 2003; 50(5):616-27.
Iasemidis, et al. Automated Seizure Prediction Paradigm. Epilepsia. 1998; vol. 39, pp. 56.
Iasemidis, et al. Chaos Theory and Epilepsy. The Neuroscientist. 1996; 2:118-126.
Iasemidis, et al. Comment on "Inability of Lyapunov exponents to predict epileptic seizures." Physical Review Letters. 2005; 94(1):019801-1.
Iasemidis, et al. Detection of the Preictal Transition State in Scalp-Sphenoidal EEG Recordings. American Clinical Neurophysiology Society Annual Meeting, Sep. 1996. pp. C206.
Iasemidis, et al. Dynamical Interaction of the Epileptogenic Focwith Extrafocal Sites in Temporal Lobe Epilepsy (TLE). Ann. Neurol. 1997; 42, pp. 429. pp. M146.
Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.
Iasemidis, et al. Localizing Preictal Temporal Lobe Spike Foci Using Phase Space Analysis. Electroencephalography and Clinical Neurophysiology. 1990; 75, pp. S63-64.
Iasemidis, et al. Long-term prospective on-line real-time seizure prediction. Clin. Neurophysiol. 2005; 116(3): 532-44.
Iasemidis, et al. Long-Time-Scale Temporo-spatial Patterns of Entertainment of Preictal Electrocorticographic Data in Human Temporal Lobe Epilepsy. Epilepsia. 1990; 31(5):621.
Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.
Iasemidis, et al. Modelling of ECoG in temporal lobe epilepsy. Biomed. Sci. Instrum. 1988; 24: 187-93.
Iasemidis, et al. Nonlinear Dynamics of EcoG Data in Temporal Lobe Epilepsy. Electroencephalography and Clinical Neurophysiology. 1998; 5, pp. 339.
Iasemidis, et al. Phase space topography and the Lyapunov exponent of electrocorticograms in partial seizures. Brain Topogr. 1990; 2(3): 187-201.
Iasemidis, et al. Preictal Entrainment of a Critical Cortical Mass is a Necessary Condition for Seizure Occurrence. Epilepsia. 1996; 37, suppl. 5. pp. 90.
Iasemidis, et al. Preictal-Postictal Vers Postictal Analysis for Epileptogenic Foc Localization. J. Clin. Neurophysiol. 1997; 14, pp. 144.
Iasemidis, et al. Quadratic binary programming and dynamic system approach to determine the predictability of epileptic seizures. Journal of Combinatorial Optimization. 2001; 5: 9-26.
Iasemidis, et al. Quantification of Hidden Time Dependencies in the EEG within the Framework of Non-Linear Dynamics. World Scientific. 1993; pp. 30-47.
Iasemidis, et al. Spatiotemporal dynamics of human epileptic seizures. World Scientific. 1996; pp. 26-30.
Iasemidis, et al. Spatiotemporal Evolution of Dynamical Measures Precedes Onset of Mesial Temporal Lobe Seizures. Epilepsia. 1994; 358, pp. 133.
Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artificial Systems. Ohmsha IOS Press. 1997; 37, pp. 81-88.).
Iasemidis, et al. The evolution with time of the spatial distribution of the largest Lyapunov exponent on the human epileptic cortex. World Scientific. 1991; pp. 49-82.
Iasemidis, et al. The Use of Dynamical Analysis of EEG Frequency Content in Seizure Prediction. American Electroencephalographic Society Annual Meeting, Oct. 1993.
Iasemidis, et al. Time Dependencies in Partial Epilepsy. 1993; 34, pp. 130-131.
Iasemidis, et al. Time dependencies in the occurrences of epileptic seizures. Epilepsy Res. 1994; 17(1): 81-94.
Iasemidis, L. D. Epileptic seizure prediction and control. IEEE Trans. Biomed. Eng. 2003; 50(5):549-58.
Jerger, et al. Early seizure detection. Journal of Clin. Neurophysiol. 2001; 18(3):259-68.
Jerger, et al. Multivariate linear discrimination of seizures. Clin. Neurophysiol. 2005; 116(3):545-51.
Jouny, et al. Characterization of epileptic seizure dynamics using Gabor atom density. Clin. Neurophysiol. 2003; 114(3):426-37.
Jouny, et al. Signal complexity and synchrony of epileptic seizures: is there an identifiable preictal period? Clin. Neurophysiol. 2005; 116(3):552-8.
Kapiris, et al. Similarities in precursory features in seismic shocks and epileptic seizures. Europhys. Lett. 2005; 69(4);657-663.
Katz, et al. Does interictal spiking change prior to seizures? Electroencephalogr. Clin. Neurophysiol. 1991; 79(2):153-6.
Kerem, et al. Forecasting epilepsy from the heart rate signal. Med. Biol. Eng. Comput. 2005; 43(2):230-9.
Khalilov, et al. Epileptogenic actions of GABA and fast oscillations in the developing hippocampus. Neuron. 2005; 48(5):787-96.
Korn, et al. Is there chaos in the brain? II. Experimental evidence and related models. C. R. Biol. 2003; 326(9):787-840.
Kraskov, A. Synchronization and Interdependence Measures and Their Application to the Electroencephalogram of Epilepsy Patients and Clustering of Data. Available at http://www.kfa-juelich.de/nic-series/volume24/nic-series-brand24.pdf. Accessed Apr. 17, 2006 (106 pp.).
Kreuz, et al. Measure profile surrogates: a method to validate the performance of epileptic seizure prediction algorithms. Phys. Rev. E. 2004; 69(6 Pt 1):061915-1-9.
Lachaux, et al. Measuring phase synchrony in brain signals. Hum. Brain Mapp. 1999; 8(4):194-208.
Lai, et al. Controlled test for predictive power of Lyapunov exponents: their inability to predict epileptic seizures. Chaos. 2004; 14(3):630-42.
Lai, et al. Inability of Lyapunov exponents to predict epileptic seizures. Phys. Rev. Lett. 2003; 91(6):068102-1-4.
Latka, et al. Wavelet analysis of epileptic spikes. Phys. Rev. E. 2003; 67(5 Pt 1):052902 (6 pages).
Le Van Quyen, et al. Anticipating epileptic seizures in real time by a non-linear analysis of similarity between EEG recordings. Neuroreport. 1999; 10(10):2149-55.
Le Van Quyen, et al. Author's second reply. The Lancet. 2003; 361:971.

(56) References Cited

OTHER PUBLICATIONS

Le Van Quyen, et al. Comparison of Hilbert transform and wavelet methods for the analysis of neuronal synchrony. J. Neurosci. Methods. 2001; 111(2):83-98.
Le Van Quyen, et al. Nonlinear analyses of interictal EEG map the brain interdependences in human focal epilepsy. Physicia D. 1999; 127:250-266.
Le Van Quyen, et al. Preictal state identification by synchronization changes in long-term intracranial EEG recordings. Clin. Neurophysiol. 2005; 116(3):559-68.
Le Van Quyen, M. Anticipating epileptic seizures: from mathematics to clinical applications. C. R. Biol. 2005; 328(2):187-98.
Lehnertz, et al. Nonlinear EEG analysis in epilepsy: its possible use for interictal foc localization, seizure anticipation, and prevention. J. Clin. Neurophysiol. 2001; 18(3):209-22.
Lehnertz, et al. Seizure prediction by nonlinear EEG analysis. IEEE Eng. Med. Biol. Mag. 2003; 22(1):57-63.
Lehnertz, et al. The First International Collaborative Workshop on Seizure Prediction: summary and data description. Clin. Neurophysiol. 2005; 116(3):493-505.
Lehnertz, K. Non-linear time series analysis of intracranial EEG recordings in patients with epilepsy—and overview. Int. J. Psychophysiol. 1999; 34(1):45-52.
Lemos, et al. The weighted average reference montage. Electroencephalogr. Clin. Neurophysiol. 1991; 70(5):361-70.
Li, et al. Fractal spectral analysis of pre-epileptic seizures in terms of critically. J. Neural Eng. 2005; 2(2):11-16.
Li, et al. Linear and nonlinear measures and seizure anticipation in temporal lobe epilepsy. J. Comput. Neurosci. 2003; 15(3):335-45.
Li, et al. Non-linear, non-invasive method for seizure anticipation in focal epilepsy. Math. Biosci. 2003; 186(1):63-77.
Litt, et al. Prediction of epileptic seizures. Lancet Neurol. 2002; 1(1):22-30.
Litt, et al. Seizure prediction and the preseizure period. Curr. Opin. Neurol. 2002; 15(2):173-7.
Maiwald, et al. Comparison of three nonlinear seizure prediction methods by means of the seizure prediction characteristic. Physica D. 2004; 194:357-368.
Mangasarian, et al. Lagrangian Support Vector Machines. Journal of Machine Learning Research. 2001; 1:161-177.
Martinerie, et al. Epileptic seizures can be anticipated by non-linear analysis. Nat. Med. 1998; 4(10):1173-6.
McSharry, et al. Comparison of predictability of epileptic seizures by linear and a nonlinear method. IEEE Trans. Biomed. Eng. 2003; 50(5):628.33.
McSharry, et al. Linear and non-linear methods for automatic seizure detection in scalp electro-encephalogram recordings. Med. Biol. Eng. Comput. 2002; 40(4):447-61.
McSharry, P. E. Detection of dynamical transitions in biomedical signals using nonlinear methods. Lecture Notes in Computer Science 2004; 3215:483-490.
Meng, et al. Gaussian mixture models of ECoG signal features for improved detection of epileptic seizures. Med. Eng. Phys. 2004; 26(5):379-93.
Mizuno-Matsumoto, et al. Wavelet-crosscorrelation analysis can help predict whether bursts of pulse stimulation will terminate after discharges. Clin. Neurophysiol. 2002; 113(1):33-42.
Mormann et al.; Seizure prediction: the long and winding road; BRAIN; vol. 130; No. 2; pp. 314-333; Sep. 28, 2006.
Mormann, et al. Automated detection of a preseizure based on a decrease in synchronization in intracranial electroencephalogram recordings from epilepsy patients. Phys. Rev. E. 2003; 67(2 Pt 1):021912-1-10.
Mormann, et al. Epileptic seizures are preceded by a decrease in synchronization. Epilepsy Res. 2003; 53(3):173-85.
Mormann, et al. Mean phase coherence as a measure for phase synchronization and its application to the EEG of epilepsy patients. Physica D. 2000; 144:358-369.
Mormann, et al. On the predictability of epileptic seizures. Clin. Neurophysiol. 2005; 116(3):569-87.
Mormann, et al. Seizure anticipation: from algorithms to clinical practice. Curr. Opin. Neurol. 2006; 19(2):187-93.
Navarro, et al. Seizure anticipation in human neocortical partial epilepsy. Brain. 2002; 125:640-55.
Navarro, et al. Seizure anticipation: do mathematical measures correlate with video-EEG evaluation? Epilepsia. 2005; 46(3):385-96.
Niederhauser, et al. Detection of seizure precursors from depth-EEG using a sign periodogram transform. IEEE Trans. Biomed. Eng. 2003; 50(4):449-58.
Nigam, et al. A neural-network-based detection of epilepsy. Neurological Research. 2004; 26(1):55-60.
Osorio, et al. Automated seizure abatement in humans using electrical stimulation. Ann. Neurol. 2005; 57(2):258-68.
Osorio, et al. Performance reassessment of a real-time seizure-detection algorithm on long ECoG series. Epilepsia. 2002; 43(12):1522-35.
Osorio, et al. Real-time automated detection and quantitative analysis of seizures and short-term prediction of clinical onset. Epilepsia. 1998; 39(6):615-27.
Ossadtchi, et al. Hidden Markov modeling of spike propagation from interictal MEG data. Phys. Med. Biol. 2005; 50(14):3447-69.
Pflieger, et al. A noninvasive method for analysis of epileptogenic brain connectivity. Presented at the American Epilepsy Society 2004 Annual meeting, New Orleans. Dec. 6, 2004. Epilepsia. 2004; 45(Suppl. 7):70-71.
Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.
Platt, et al. Large Margin DAGs for Multiclass Classification. S.A. Solla. T.K. Leen and K.R. Muller (eds.). 2000; pp. 547-553.
Platt, J. C. Using Analytic QP and Sparseness to Speed Training of Support Vector Machines. Advances in Neural Information Processing Systems. 1999; 11:557-563.
Protopopescu, et al. Epileptic event forewarning from scalp EEG. J. Clin. Neurophysiol. 2001; 18(3):223-45.
Rahimi, et al. On the Effectiveness of Aluminum Foil Helmets; An empirical Study Available at http://people.csail.mit.edu/rahimi/helmet/. Accessed Mar. 2, 2006.
Robinson, et al. Steady States and Global Dynamics of Electrical Activity in the Cerebral Coretex. Phys. Rev. E. 1998; (58):3557-3571.
Rothman et al.; Local Cooling: a therapy for intractable neocortical epilepsy; Epilepsy Currents; vol. 3; No. 5; pp. 153-156; Sep./Oct. 2003.
Rudrauf, et al. Frequency flows and the time-frequency dynamics of multivariate phase synchronization in brain signals. NeuroImage. 2005. (19 pages).
Saab, et al. A system to detect the onset of epileptic seizures in scalp EEG. Clin. Neurophysiol. 2005; 116:427-442.
Sackellares et al. Computer-Assisted Seizure Detection Based on Quantitative Dynamical Measures. American Electroencephalographic Society Annual Meeting, Sep. 1994.
Sackellares et al. Dynamical Studies of Human Hippocampin Limbic Epilepsy. Neurology. 1995; 45, Suppl. 4, p. A 404.
Sackellares et al. Epileptic Seizures as Neural Resetting Mechanisms. Epilepsia. 1997; vol. 38, Sup. 3.
Sackellares et al. Measurement of Chaos to Localize Seizure Onset. Epilepsia. 1989; 30(5):663.
Sackellares et al. Predictability Analysis for an Automated Seizure Prediction algorrithim; Journal of Clinical Neurophysiology; vol. 23; No. 6; pp. 509-520; Dec. 2006.
Sackellares et al. Relationship Between Hippocampal Atrophy and Dynamical Measures of EEG in Depth Electrode Recordings. American Electroencephalographic Society Annual Meeting, Sep. 1995. pp. A105.
Sackellares, J. C. Epilepsy—when chaos fails. In: chaos in the brain? Eds. K. Lehnertz & C.E. Eiger. World Scientific. 2000 (22 pages).
Salant, et al. Prediction of epileptic seizures from two-channel EEG. Med. Biol. Eng. Comput. 1998; 36(5):549-56.

(56) References Cited

OTHER PUBLICATIONS

Schelter et al.; Testing statistical significance of multivariate time series analysis techniques for epileptic seizure prediction; Chaos;: An Interdisciplinary Journal of Nonlinear Science; vol. 16; No. 013108; pp. 1-10; Jan. 2006.
Schelter, et al. Testing for directed influences among neural signals using partial directed coherence. J. Neurosci. Methods. 2006; 152-(1-2):210-9.
Schindler, et al. EEG analysis with simulated neuronal cell models helps to detect pre-seizure changes. Clin. Neurophysiol. 2002; 113(4):604-14.
Schwartzkroin, P. Origins of the Epileptic State. Epilepsia. 1997; 38, supply. 8, pp. 853-858.
Sheridan, T. Humans and Automation. NY: John Wiley. 2002.
Shoeb et al. Patient-specific seizure detection. MIT Computer Science and Artificial Intelligence Laboratory. 2004; pp. 193-194.
Snyder et al; The statistics of a practical seizure warning system; Journal of Neural Engineering; vol. 5; pp. 392-401; 2008.
Spector et al.; High and Low Perceived Self-Control of Epileptic Seizures; Epilepsia, vol. 42(4), Apr. 2001; pp. 556-564.
Staba, et al. Quantitative analysis of high-frequency oscillations (80-500 Hz) recorded in human epileptic hippocampand entorhinal cortex. J. Neurophysiol. 2002; 88(4): 1743-52.
Stefanski, et al. Using chaos synchronization to estimate the largest Lyapunov exponent of nonsmooth systems. discrete Dynamics in Nature and Society. 2000; 4:207-215.
Subasi, et al. Classification of EEG signals using neural network and logistic regression. Computer Methods Programs Biomed. 2005; 78(2):87-99.
Szoka et al. Procedure for preparation of liposomes with large internal aqueospace and high capture volume by reverse phase evaporation. 1978 Proc. Natl Acad. Sci. USA. 75: 4194-4198.
Tass, et al. Detection of n: m Phase Locking from Noisy Data: Application to Magnetoencephalography. Physical Review Letters. 1998; 81(15):3291-3294.
Terry, et al. An improved algorithm for the detection of dynamical interdependence in bivariate time-series. Biol. Cybern. 2003; 88(2):129-36.
Tetzlaff, et al. Cellular neural networks (CNN) with linear weight functions for a prediction of epileptic seizures. Int'l J. of Neural Systems. 2003; 13(6):489-498.
Theiler, et al. Testing for non-linearity in time series: the method of surrogate data. Physica D. 1992; 58:77-94.
Tsakalis, K. S. Prediction and control of epileptic seizures: Coupled oscillator models. Arizona State University. (Slide: 53 pages) (No date).
Van Drongelen, et al. Seizure anticipation in pediatric epilepsy: use of Kolmogorov entropy. Pediatr. Neurol. 2003; 29(3): 207-13.
Van Putten, M. Nearest neighbor phase synchronization as a measure to detect seizure activity from scalp EEG recordings. J. Clin. Neurophysiol. 2003; 20(5):320-5.
Venugopal, et al. A new approach towards predictability of epileptic seizures: KLT dimension. Biomed Sci. Instrum. 2003; 39:123-8.
Vonck, et al. Long-term amygdalohippocampal stimulation for refractory temporal lobe epilepsy. Ann. Neurol. 2002; 52(5):556-65.
Vonck, et al. Long-term deep brain stimulation for refractory temporal lobe epilepsy. Epilepsia. 2005; 46 (Suppl 5):98-9.
Vonck, et al. Neurostimulation for refractory epilepsy. Acta. Neurol. Belg. 2003; 103(4):213-7.
Weiss, P. Seizure prelude found by chaos calculation. Science News. 1998; 153(20):326.
Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.
Widman, et al. Reduced signal complexity of intracellular recordings: a precursor for epileptiform activity? Brain Res. 1999; 836(1-2):156-63.
Winterhalder, et al. Sensitivity and specificity of coherence and phase synchronization analysis. (In Press) Phys. Lett. A. 2006.
Winterhalder, et al. The seizure prediction characteristic: a general framework to assess and compare seizure prediction methods. Epilepsy Behav. 2003; 4(3):318-25.
Wong et al.; A stochastic framework for evaluating seizure prediction algorithms using hidden markov models; Journal of Neurophysiology; vol. 97, No. 3; pp. 2525-2532; Oct. 4, 2006.
Yang et al.; Testing whether a prediction scheme is better than guess; Ch. 14 in Quantitative Neuroscience: Models, Algorithms, Diagnostics, and Therapeutic Applications; pp. 252-262; 2004.
Yang, et al. A supervised feature subset selection technique for multivariate time series. Available at http://infolab.usc.edu/DocsDemos/fsdm05.pdf. Accessed Mar. 2, 2006.
Yang, et al. CLe Ver: A feature subset selection technique for multivariate time series. T.B. Ho, D. Cheung, and H. Liu (Eds.): PAKDD. 2005; LNAI 3518: 516-522.
Yang, et al. Relation between Responsiveness to Neurotransmitters and Complexity of Epileptiform Activity in Rat Hippocampal CA1 Neurons. Epilepsia. 2002; 43(11):1330-1336.
Yatsenko, et al. Geometric Models, Fiber Bundles, and Biomedical Applications. Proceedings of Institute of Mathematics of NAS of Ukraine. 2004; 50 (Part 3):1518R1525.
Zaveri et al. Time-Frequency Analyses of Nonstationary Brain Signals. Electroencephalography and Clinical Neurophysiology. 1991; 79, pp. 28P-29P).
Zhang, et al. High-resolution EEG: cortical potential imaging of interictal spikes. Clin. Neurophysiol. 2003; 114(10):1963-73.

\* cited by examiner

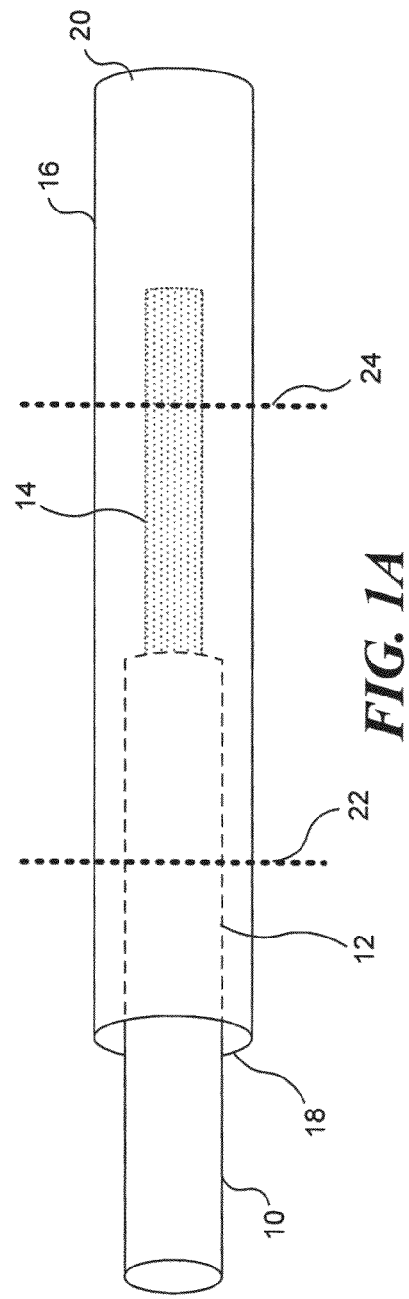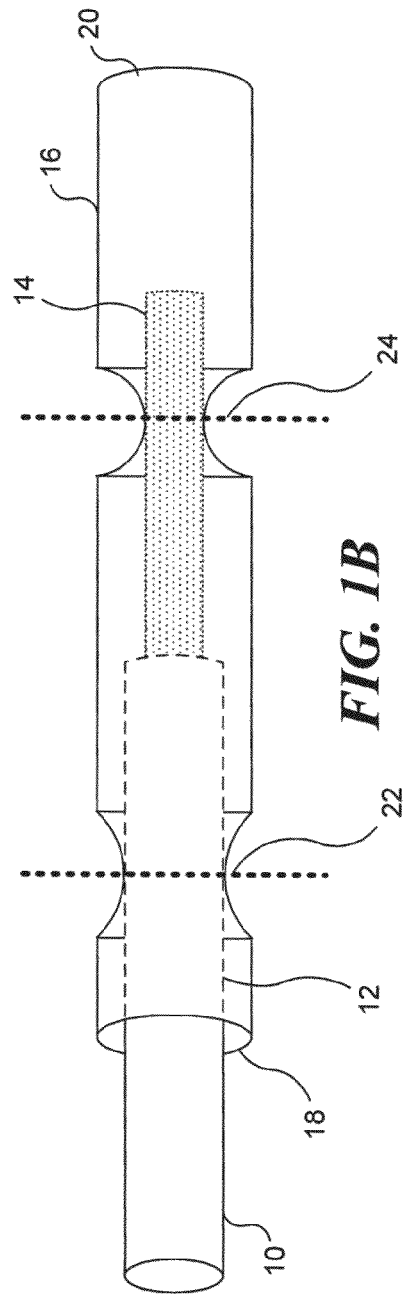

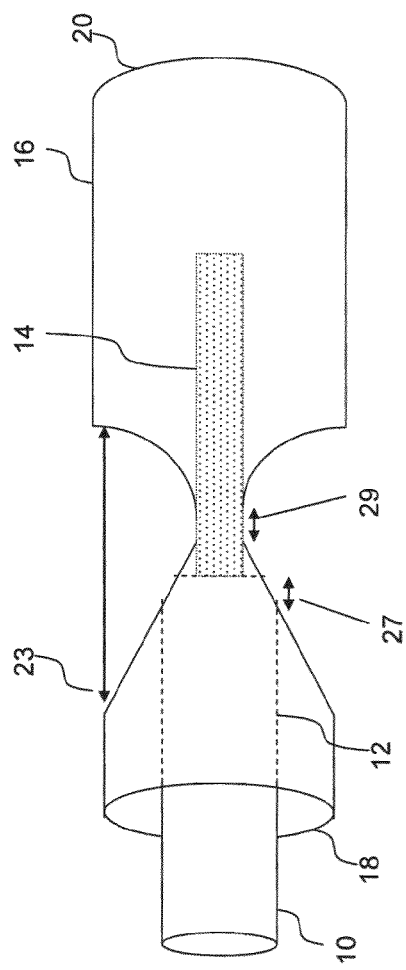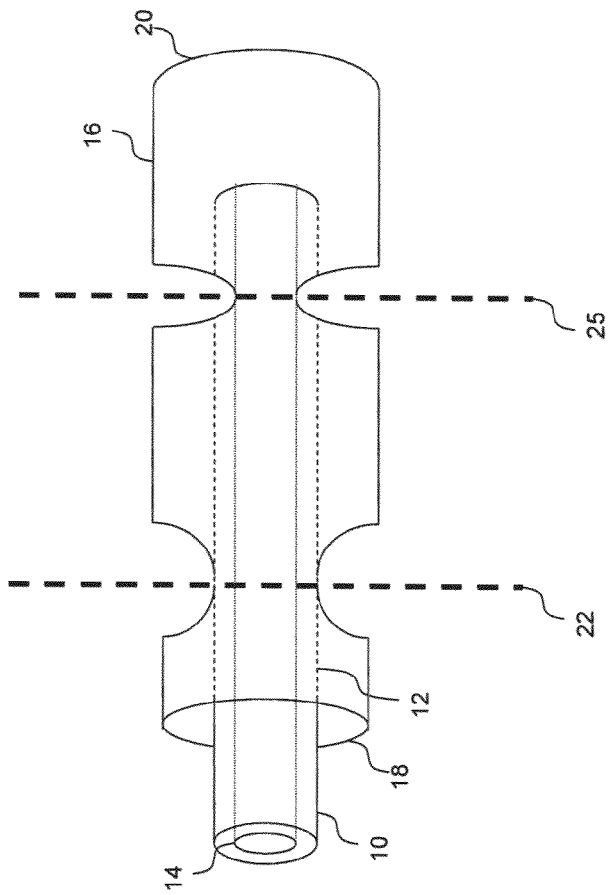

MEDICAL LEAD TERMINATION SLEEVE FOR IMPLANTABLE MEDICAL DEVICES

CROSS-REFERENCE TO RELATED APPLICATIONS

This application is a continuation of U.S. patent application Ser. No. 12/685,543 filed Jan. 11, 2010, which claims the benefit of U.S. Provisional Application No. 61/143,571, filed Jan. 9, 2009, both of which are incorporated herein by reference in their entireties.

BACKGROUND OF THE INVENTION

Implantable medical devices often include an electrode to which a conductive wire is attached. Conventionally, medical lead wires are simply welded to an electrode. However, there are several disadvantages to this technique: (1) lead wire and electrode materials are often dissimilar and are at risk of sustaining galvanic corrosion when used together in an in vivo environment in which they are exposed to bodily fluids; (2) if lead wire and electrode materials are dissimilar, welds between such dissimilar materials are typically of lower quality than welds between similar materials; (3) lead wire diameters for implanted medical devices are generally small, so that properly welding these small-diameter lead wires to electrodes can present manufacturing challenges; and (4) laser spot welding of such relatively small diameter lead wires can lead to poor quality welds.

With respect to the dissimilar materials noted above, because lead wires and electrodes serve different functions, the properties desired for the lead wire material may be different than the properties desired for the electrode material. Accordingly, a desirable material for a lead wire might not be desirable for an electrode. For example, lead wires for implanted medical devices must exhibit a high tensile strength, to withstand repeated bending cycles without breakage, and a nickel cobalt alloy (MP35N) is often selected as a material for lead wires. Because the lead wires are encapsulated in an insulating polymer cover, the biocompatibility of the lead wire material is generally less important than the material's tensile strength. The electrodes, however, are often placed in contact with bodily fluids or tissue, and thus, the biocompatibility of the material from which the electrodes are formed is quite important. Platinum-iridium alloys are biocompatible, inert, and very conductive; thus, electrodes in medical devices are often made from such alloys.

Where two different metals are connected together and exposed to a common electrolyte (in the case of an implanted medical device, bodily fluid represents the common electrolyte), there exists a risk of galvanic corrosion, which is highly undesirable in the context of the long term reliability of an implantable medical device.

With respect to the manufacturing challenges noted above, in the context of implanted medical devices, lead wire diameters can be as small as about 0.003 inches (~75 microns), which is approximately the diameter of a single human hair, or even as little as 0.001 inches. Aligning such small diameter lead wires for welding on a relatively larger electrode can be challenging, especially with regards to multifilar wires having eight or more individual wire strands.

With respect to problems associated with laser spot welding of relatively small diameter lead wires, conventional laser spot welding does not utilize an additional filler material, so the material that is liquefied to make the weld is produced by melting the components being welded together. In the case of a relatively small diameter lead wire, the lead wire will melt well before the electrode (because the electrode is more massive than the lead wire), and the lead wire can either melt entirely (leading to immediate failure of the weld), or the diameter of the lead wire can be greatly reduced when melted, generating a weak spot that is prone to failure. A further problem is that where the lead wire material has been initially heat treated, the heat from the welding operation can adversely affect the initial heat treatment, reducing the strength of the lead wire.

Based on the disadvantages of the conventional approach used to join lead wires to electrodes discussed above, it would clearly be desirable to provide alternative techniques for coupling lead wires to electrodes in implantable medical devices.

SUMMARY OF THE INVENTION

A termination sleeve is provided that is crimped onto a distal end of an electrical lead wire, so that the termination sleeve can then be welded to an electrode. Other embodiments are directed to an electrical lead wire and electrode in a combination suitable for use with implanted medical devices, and to a method for coupling an electrical lead wire and electrode to achieve a robust electrical connection suitable for use with such medical devices. An exemplary electrical lead wire is optimized for strength, and exemplary electrodes and termination sleeves are optimized for biocompatibility and corrosion resistance—in accord with this novel approach.

The termination sleeve can be fabricated using the same material that is used to fabricate the electrode, thereby eliminating the risk of galvanic corrosion and ensuring that a high quality weld between the termination sleeve and the electrode can be obtained. Because the termination sleeve will have more mass than the electrical lead wire, laser spot welding can be employed without encountering the disadvantages noted above when welding a lead wire to an electrode in the conventional manner. Further, the relatively larger termination sleeve will be easier to manipulate during the manufacturing process than the smaller electrical lead wires typically used in the prior approach.

Significantly, the termination sleeve can be fabricated to have a longitudinal length that is sufficient to enable the termination sleeve to engage the distal end of the electrical lead wire at two spaced-apart locations, and a distal end of the termination sleeve is sealed (i.e., the termination sleeve can be open at only a proximal end, so the lead wire can only be inserted into the termination sleeve via the proximal end). Further, an inside diameter of the termination sleeve can be sufficient to accommodate the electrical lead wire while it is still encapsulated within its insulating polymer cover. To attach the termination sleeve to the electrical lead wire, a portion of the electrical lead wire's insulating polymer cover can be removed, exposing the bare lead wire. To achieve adequate sealing, the portion with the cover removed should be shorter than the termination sleeve itself. The distal end of the lead wire is then inserted into the proximal end (i.e., the open end) of the termination sleeve, so that at least a portion of the electrical lead wire that is still covered with the insulating polymer cover is introduced into the termination sleeve. With respect to the length of the electrical lead wire introduced into the termination sleeve, the portion of the electrical lead wire still covered with the insulating polymer will then be disposed relatively closer to the proximal end (i.e., the open end) of the termination sleeve, while the portion of the electrical lead wire that is bare or not covered with the insulating polymer will be disposed relatively closer to the distal end (i.e., the closed end) of the termination sleeve. A first segment of the termination sleeve overlaying the portion of the electrical lead wire still covered with the insulating polymer can be compressed (i.e., crimped) to sealingly engage the portion of the electrical lead wire still covered with the insulating polymer, and a second segment of the termination sleeve overlaying the portion of the electrical lead wire not covered with the insulating polymer can also be compressed (i.e., crimped) to engage the portion of the electrical lead wire not covered with the insulating polymer.

Thus, the first compressed segment of the termination sleeve engages the portion of the electrical lead wire still covered with the insulating polymer to seal the interior of the termination sleeve, thereby protecting the portion of the electrical lead wire not covered with the insulating polymer from exposure to the in vivo environment (such as bodily fluids). In other words, the insulating polymer under compression acts like a radial gasket or sealing member between metallic components. The second compressed segment of the termination sleeve engages the portion of the electrical lead wire not covered with the insulating polymer, thereby electrically coupling the electrical lead wire to the termination sleeve.

The termination sleeve can then be laser spot welded or otherwise electrically coupled to the electrode (recognizing that the termination sleeve can be coupled to other conductive elements, such as a contact spring or a radial connector. While laser spot welding represents an exemplary technique to attach the termination sleeve to the electrode, it should be recognized that any of several other suitable techniques can instead be employed. Such other techniques include, but are not limited to, other types of welding, crimping, diffusion bonding, capture with threaded or non-threaded fasteners, and the use of conductive adhesives (while less preferred, non-conductive adhesives can also be employed, so long as some portion of the termination sleeve is electrically coupled to the electrode).

In at least one embodiment, the termination sleeve and the electrode comprise an alloy of platinum and iridium.

A related exemplary embodiment employs a modified compression or crimping technique. The first and second discrete crimping techniques in the aforementioned section are replaced by a single crimping technique which allows for the continuous crimp allowing for the termination sleeve to engage the portion of the electrical lead wire still covered with the insulating polymer to seal the interior of the sleeve while also allowing for the termination sleeve to engage the portion of the electrical lead wire not covered with the insulating polymer, thereby electrically coupling the electrical lead wire to the termination sleeve. This embodiment potentially has the advantage of requiring only a single crimping step as opposed to the aforementioned process utilizing two crimping steps.

Another related exemplary embodiment employs a modified compression or crimping technique that makes it possible to eliminate the step of removing the insulating polymer protecting layer that covers the medical lead conductive element. A first segment of the termination sleeve can be compressed to sealingly engage the portion of the electrical lead wire covered with the insulating polymer, and a second segment of the termination sleeve also overlaying the electrical lead wire covered with the insulating polymer is compressed with a more focused localized force in order to displace the insulating polymer so as to engage the portion of the electrical lead wire. This more focused localized force, which allows the termination sleeve to conductively engage the electrical lead wire by forcibly displacing the insulating polymer, can be achieved by any of the following: (i) increased compression force; (ii) narrower compression area; (iii) a feature located on the inside diameter of the termination sleeve which serves to localize the crimping force such as a protruded internal rib; and (iv) combinations thereof.

This Summary has been provided to introduce a few concepts in a simplified form that are further described in detail below in the Description and illustrated in the accompanying Drawings. The Summary is not intended to limit the scope of the invention, which is defined solely by the claims attached hereto.

BRIEF DESCRIPTION OF THE DRAWINGS

FIG. 1A illustrates a medical lead wire inserted into an exemplary termination sleeve in accordance with the concepts disclosed herein, wherein the termination sleeve includes an open proximal end and a closed distal end;

FIG. 1B illustrates the medical lead wire and termination sleeve combination of FIG. 1A, after the termination sleeve has been modified to fastenably engage the medical lead wire at a first location and a second location, the termination sleeve sealingly engaging an insulating protective cover of the medical lead wire at the first location, and conductively engaging the medical lead wire at the second location;

FIG. 1C illustrates an exemplary termination sleeve, which is sealed using a single crimp;

FIG. 1D illustrates another exemplary termination sleeve;

DETAILED DESCRIPTION OF THE INVENTION

Figure 2:
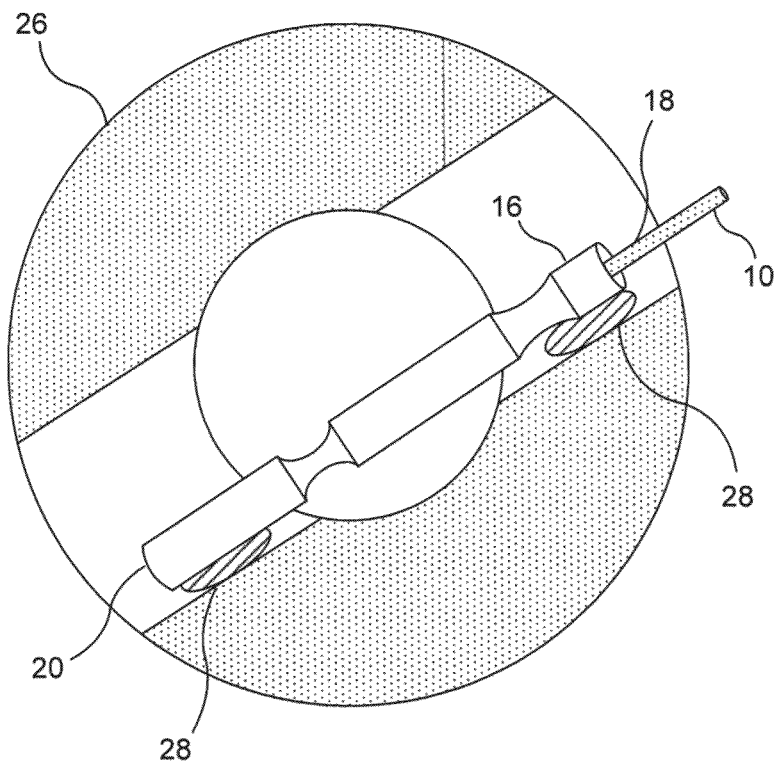
FIG. 2 illustrates a termination sleeve containing a distal end of a lead wire spot welded to an electrode.

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

First Exemplary Embodiment of Termination Sleeve

FIG. 1A illustrates a lead wire inserted into an exemplary termination sleeve for use with implantable medical devices, wherein the termination sleeve includes an open proximal end and a closed distal end, relative to the medical lead wire. FIG. 1B illustrates the medical lead wire and termination sleeve combination of FIG. 1A, after the termination sleeve has been modified to engage the medical lead wire at a first location and a second location, the termination sleeve sealingly engaging an insulating protective cover of the medical lead wire at the first location, and conductively engaging the medical lead wire at the second location, fastening the medical lead wire within the termination sleeve and making an electrical connection between the two components. The termination sleeve can next be electrically and physically coupled to an electrode, as shown in FIG. 2. Significantly, the relatively larger termination sleeve is easier to manipulate than the relatively smaller medical lead wire, thus facilitating manufacture of an implantable medical device.

With respect to exemplary materials for the medical lead wire, the termination sleeve, and the electrode, it should be noted that preferable material properties for the medical lead wire may be different than the material properties preferred for the termination sleeve and the electrode. Specifically, in some medical applications, the medical lead wire (which can include either a singular or multifilar conductor) can be intended for long term implantation within a patient's body, and may be subject to physical stress due to frequent body motion. In such an application, it is extremely important that the wire(s) or filar(s) do not break during such use. Thus, preferable material properties for implantable lead wires include good electrical conductivity, relatively high tensile strength, and relatively high resistance to metal fatigue. Any of a variety of materials may be used for the implantable lead wires, depending on the application. Metal alloys that may be used in medical lead wires include, but are not limited to, stainless steels, and superalloys containing nickel, cobalt, chromium, and molybdenum. Such superalloys are marketed under various trademarks, including 35N LT™, Eigiloy™, and MP35N™. In addition to having high tensile strength, these nonmagnetic and conductive nickel-cobalt-chromium-molybdenum alloys possess good ductility and toughness and are relatively inert and biocompatible. Metal matrix composites or metal-to-metal composites may be used, such as drawn filled tube composites, e.g., DFT wire produced by Fort Wayne Metal of Fort Wayne, Ind. These conductive materials are employed for the inner conductive core of medical lead wires and are covered with an insulating layer, such as a polymer material. Ethylene tetrafluoroethylene (ETFE) and polytetrafluoroethylene (PTFE) represent exemplary, but not limiting polymers that can be used for the insulating layer or jacket. The ETFE or PTFE jacket serves to both electrically insulate the inner conductor as well as seal the inner conductor, so that the inner conductor is not exposed to bodily fluids.

In summary, typical important physical properties for the medical lead wires include good electrical conductivity, relatively high tensile strength, and relatively high resistance to metal fatigue, as well as biocompatibility.

With respect to an implanted electrode which is exposed to an in vivo environment, it is important for the electrode material to be highly biocompatible and inert, with less emphasis upon tensile strength. In addition, the material must also be sufficiently conductive so as to effectively conduct the detected signals. Exemplary, but not limiting electrode materials include inert or biocompatible metals such as platinum, gold, and palladium, including alloys thereof. For example, a good choice for such a material would be an alloy of platinum and iridium.

In prior art implantable medical devices, the insulating cover of the medical lead wire is removed from the distal end of the medical lead wire, and the exposed inner conductor is then welded to the electrode. Often, the inner conductor and electrode are made of dissimilar materials, leading to relatively weaker welds. Furthermore, the weld is exposed to bodily fluids, and the use of dissimilar metals in such an in vivo environment can lead to a heightened risk of galvanic corrosion. In accordance with embodiments of the present invention, these deficiencies may be addressed by employing a termination sleeve having a closed distal end. Exemplary termination sleeves are formed from the same material (or a chemically similar material) as the electrode, which can provide better quality, more reliable welds between the termination sleeve and the conductor, and reduces or eliminates the risk of galvanic corrosion. Furthermore, the termination sleeve defines an inner volume that can be isolated from the in vivo environment, and thus, the exposed end of the medical lead wire as well as the electrical connection between the medical lead wire and the termination sleeve within this inner volume can be isolated from the in vivo environment.

Referring once again to FIGS. 1A and 1B, a first exemplary embodiment of a termination sleeve in accordance with the concepts disclosed herein is illustrated. A termination sleeve 16 includes an open proximal end 18 and a closed distal end 20. An elongate hollow body extends between proximal end 18 and distal end 20. Several different techniques can be employed to achieve a seal at distal end 20, including originally manufacturing the termination sleeve with a closed distal end, mechanically modifying an open distal end (such as by laser melting, crimping or otherwise deforming the distal end of the termination sleeve), and by the use of a sealing member. Laser melting a tip of the distal end of the termination sleeve represents an exemplary, but not limiting, mechanical modification. A metal ball welded into an opening at the distal end represents an exemplary sealing member, although it should be recognized that other sealing members (such as a polymer plug adhesively secured to the distal end of the termination sleeve) can be employed.

As noted above, in an exemplary embodiment, the termination sleeve and the electrode to which the termination sleeve will be attached can be made from similar materials (such as an alloy of platinum and iridium). First, a portion of insulating cover 12 is removed from a distal end of a medical lead wire 10 to expose or lay bare a short length of an inner conductor 14. Next, the exposed distal end of the medical lead wire 10 is inserted into termination sleeve 16. Termination sleeve 16 is crimped in two locations—a first location 22 that is disposed closer to proximal end 18 than to distal end 20, and a second location 24 that is disposed toward a center of termination sleeve 16. First location 22 is selected such that it overlays a portion of medical lead wire 10 still covered by insulating cover 12. Selectively deforming or mechanically modifying the termination sleeve at location 22 causes the termination sleeve to compress and sealingly engage the insulating cover underlying location 22, which creates a seal between the termination sleeve 16 and insulating cover 12 to exclude bodily or other types of fluid in which the termination sleeve is disposed from reaching the inner conductor. This seal thus isolates an inner volume in the termination sleeve extending between location 22 and the closed distal end of the termination sleeve. Second location 24 is selected such that second location 24 overlays a portion of medical lead wire 10 corresponding to exposed inner conductor 14. Selectively deforming or mechanically modifying the termination sleeve at second location 24 will cause the termination sleeve to compress and conductively engage the inner conductor underlying second location 24, to electrically couple the medical lead wire to the termination sleeve. Significantly, second location 24 is disposed between first location 22 and closed distal end 20, so that the electrical connection between the inner conductor and the termination sleeve is isolated from an in vivo environment to which the termination sleeve might be exposed. This isolation prevents exposure of the contact between the inner conductor and the termination sleeve (which are likely to be fabricated using different materials, generally as discussed above) to bodily fluids, and significantly reduces the risk of galvanic corrosion.

FIG. 1A illustrates the termination sleeve after the medical lead wire has been inserted into the termination sleeve, but before the termination sleeve has been modified to physically couple with the medical lead wire. FIG. 1B illustrates the termination sleeve after the termination sleeve has been modified to physically couple with the medical lead wire. It should be noted that the relative sizes of the termination sleeve, the insulating cover, and the inner conductor of the medical lead wire are not shown on scale and are not limiting. Further, the relative positions, shapes, and sizes of the modifications to the termination sleeve shown in FIG. 1B are intended to be exemplary, and not limiting.

A common technique for selectively deforming or mechanically modifying the termination sleeve is crimping (the term crimping should be understood to encompass radial crimping, conical crimping, and crimping from opposite sides). Other techniques that enable deformation of the termination sleeve to engage the medical lead wire that is inserted therein, including but not limited to swaging techniques, can alternatively be employed for this purpose. Swaging may be the preferred compression technique in many applications. Swaging can produce a smoother and more consistently cylindrical outer surface as compared to many crimp techniques which leave noted depressions in the surface. A smoother, more uniform surface may be favorable for secondary operations such as laser welding.

The relative positions of first and second locations 22 and 24 may vary depending on the application. In some embodiments, the relative positions can be variable as long as second location 24 is disposed between first location 22 and the closed distal end of the termination sleeve, and first location 22 overlays a portion of medical lead wire 10 that is covered by insulating cover 12, and second location 24 overlays a portion of medical lead wire 10 not covered by insulating cover 12 (i.e., second location 24 overlays exposed inner conductor 14). First location 22 can be inset from proximal end 18 any amount that enables the required mechanical modifications to be implemented at first and second locations 22 and 24 without interference.

While the termination sleeve of FIG. 1A exhibits a single inner diameter (the different inner diameters shown in FIG. 1B having been achieved by selectively deforming the termination sleeve; noting that while not specifically shown in the Figures, termination sleeve 16 is a tubular structure exhibiting different inner diameters and outer diameters), it should be recognized that the termination sleeve can be initially configured to include a plurality of different inner diameters. For example, the termination sleeve can be configured to have an inner diameter slightly larger than the diameter of the insulating cover at first location 22 and smaller, but slightly larger than the diameter of the inner conductor at second location 24, such that a relatively small degree of deformation or no deformation is required for the termination sleeve to be fastened onto the medical lead wire at each location. The extent of these different dimensions along a longitudinal axis of the termination sleeve can be varied as desired and appropriate.

Employing a termination sleeve made out of the same material as the electrode to which the termination sleeve will be attached may offer the following advantages: (1) reducing or substantially eliminating the risk of galvanic metal corrosion; and (2) enabling higher quality welds to connect the termination sleeve to the electrode to be achieved compared to welds between dissimilar metals. Welding a termination sleeve to an electrode instead of welding the medical lead wire directly to the electrode may offer the following advantages: (1) manufacturing may be simplified because the use of a relatively larger and rigid termination sleeve is easier to manipulate than the relatively smaller medical lead wire; and, (2) spot welding the relatively larger termination sleeve to the electrode without the use of a filler results in a more robust weld than can be achieved by spot welding the relatively smaller medical lead wire to the electrode without using a filler. The relatively larger termination sleeve may be provided with sufficient mass such that a portion of the termination sleeve can be melted to achieve the weld without sacrificing the structural integrity of the termination sleeve, whereas melting any of the relatively smaller medical lead wire inner conductor could undesirably weaken the medical lead wire. Referring to FIG. 2, termination sleeve 16 is shown after being physically and electrically coupled to an electrode 26 at spot welds 28.

As noted above, using a termination sleeve enables an inner volume of the termination sleeve to be isolated from the in vivo environment when the termination sleeve is properly attached to the medical lead wire. The isolated inner volume extends between the first location where the termination sleeve sealingly engages the insulating protective cover of the medical lead wire, and the sealed distal end of the termination sleeve, such that the second location where the termination sleeve conductively engages the medical lead wire is disposed within the isolated volume.

FIG. 1C illustrates an alternative exemplary embodiment wherein a tapered crimp 23 replaces the need for two separate crimps in two locations as shown in FIG. 1B. In FIG. 1C, a portion of insulating cover 12 is removed from the distal end of medical lead wire 10, such that a length of exposed inner conductor 14 is less than a length of terminal sleeve 16. Tapered crimp 23 is applied to terminal sleeve 16 such that it overlays both exposed inner conductor 14 as well as the insulated portion of conductor 12. The tapered crimp is applied such that it straddles the section of the medical lead where: (i) a proximal portion 27 of tapered crimp 23 creates a seal between termination sleeve 16 and insulating cover 12 to exclude ambient bodily or other types of fluid from reaching inner conductor 14; and (ii) a distal portion 29 of tapered crimp 23 conductively engages exposed inner conductor 14 of the medical lead such that the electrical connection is isolated from an in vivo environment to which the termination sleeve might be exposed.

FIG. 1D illustrates an exemplary termination sleeve, which is sealed such that an inner volume of the termination sleeve is isolated from an in vivo environment when the termination sleeve is properly attached to a medical lead wire. The method of sealingly engaging insulating cover 12 is accomplished by proximal crimp 22. The method of conductively engaging inner conductor 14 of the medical lead wire is accomplished via distal crimp 25 in termination sleeve 16. This crimp is performed with increased force, and/or more localized force, thereby allowing termination sleeve 16 to conductively engage inner conductor 14 of the medical lead wire by forcibly displacing the insulating polymer covering inner conductor 14, such that a portion of insulating cover 12 need not be removed prior to the crimping processes.

Figure 3:
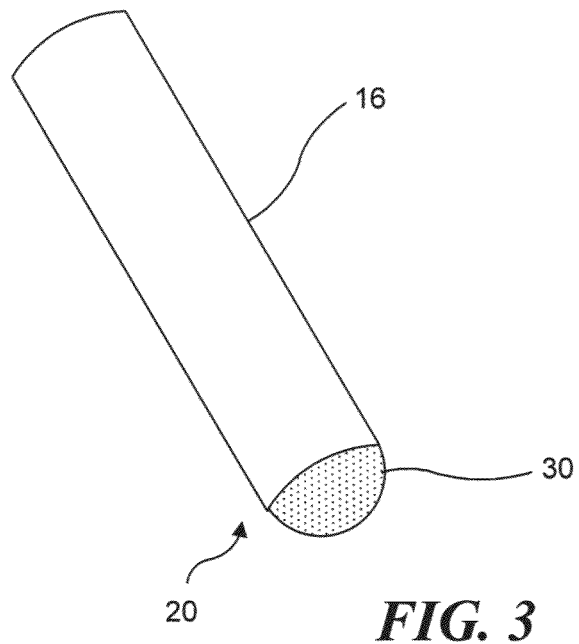
FIG. 3 illustrates a distal end of an exemplary termination sleeve.

FIG. 3 illustrates an exemplary technique for sealing distal end 20 of termination sleeve 16 by plugging a distal opening in the termination sleeve with a sealing member 30. As noted above, a spherical plug or ball made of the same material as the cylindrical body of the termination sleeve can be welded to the body of the termination sleeve to seal the distal end. Additionally, the distal end may simply be melted closed, using, e.g., laser welding. It should be recognized that welding represents only an exemplary technique for sealing the distal end with the plug or ball, since other attachment techniques can instead be employed, such as using a suitable adhesive, or achieving an interference fit between the sealing member and the termination sleeve, or combinations thereof. Further, as noted above, the termination sleeve can be initially manufactured with a sealed distal end, or the seal at the distal end can be achieved by mechanically modifying the termination sleeve. While the distal end of the termination sleeve can be sealed after the termination sleeve has been fastened to the medical lead wire, as discussed above, if the distal end of the termination sleeve is closed with a sealing member as shown in FIG. 3, it will likely be more convenient to close the distal end before attaching the termination sleeve to the medical lead wire. It should be understood that the concepts disclosed herein encompass both techniques.

Because insulating cover 12 (comprising, e.g., a polymer) will likely have a lower melting point and flash point than inner conductor 14, removing the insulating cover from just the portion of the medical lead wire that will be disposed at second location 24, while leaving the insulating cover intact at the portion of the medical lead wire that will be disposed at third location 25 can be achieved by selectively heating only the portion of the medical lead wire that will be disposed at second location 24. This selective heating can be applied using a laser or heating element (i.e., a fine metal wire or needle point that is heated with an electrical current or by exposure to an open flame or other heat source). It may be desirable for the heat to be selectively applied above the melting point of the polymer and below the level at which the inner conductor might be damaged. It should be recognized that in addition to, or in combination with using heat to selectively remove the insulating cover at the desired location, mechanical removal can also be employed, e.g., by cutting through only the insulating layer, so that the insulating layer can be peeled away from the inner conductor.

Figure 4:
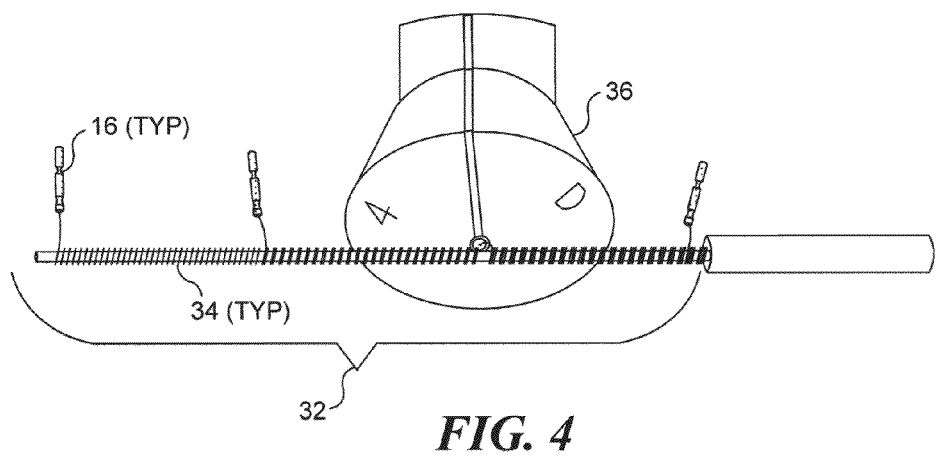
FIG. 4 illustrates an exemplary multi-filar wire, where a distal end of each individual lead wire is inserted into a termination sleeve.

While the termination sleeves disclosed herein can be employed with devices including only a single medical lead wire, it should be recognized that many devices require a plurality of lead wires, and that the concepts disclosed herein can be applied to such devices as well. FIG. 4 illustrates an exemplary multi-filar wire, where a distal end of each individual lead wire is inserted into a termination sleeve in accord with the concepts disclosed herein. A multifilar wire 32 includes four separate jacketed wires 34 that are coiled together. A crimping collar 36 is shown, and it is noted that radial crimping is one technique that can be used to fasten the termination sleeve onto a distal end of a lead wire, generally as discussed above. It should be recognized that the termination sleeve can be fastened to the lead wire using any of the following techniques: (1) using a single conical tapered crimp; (2) using a multiple profile crimp in which either the crimping tool has two different profiles optimized for both the inner conductor and the insulating cover, or the termination sleeve itself has two profile inside diameters optimized for crimping both onto the insulating cover and the inner conductor; and, (3) a swaging technique that replaces the crimping process. Still other compression techniques are contemplated.

Figure 5E:
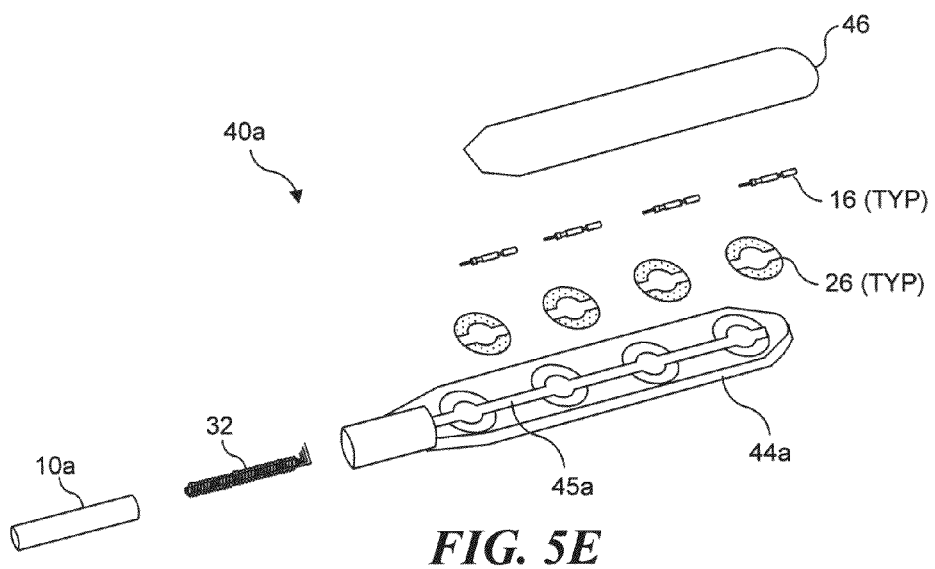
FIG. 5E illustrates an exploded view of an alternative distal strip electrode array, which directs a multifilar wire serving the individual electrode contacts through the center of the electrode contacts via a channel disposed along a central axis of the electrode body.
Figure 5A:
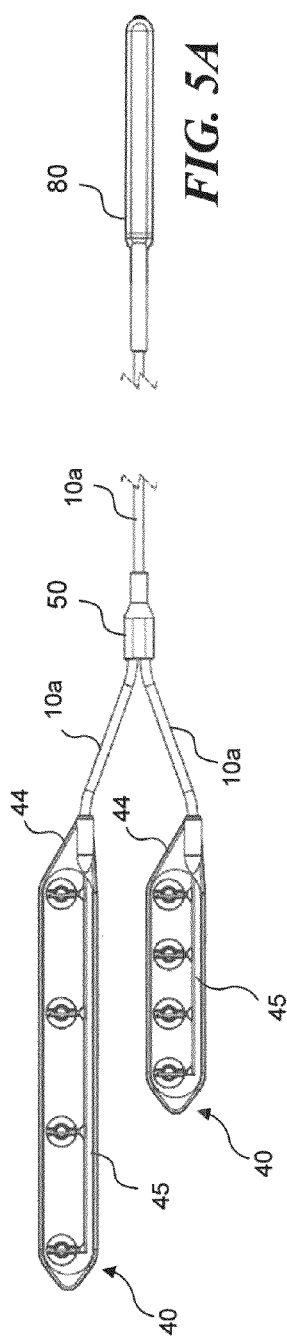
FIG. 5A is a top view of an exemplary implantable medical lead assembly including a proximal connector to be connected to an implanted medical device and a plurality of electrode arrays, each having electrode contacts and termination sleeves.
Figure 5B:
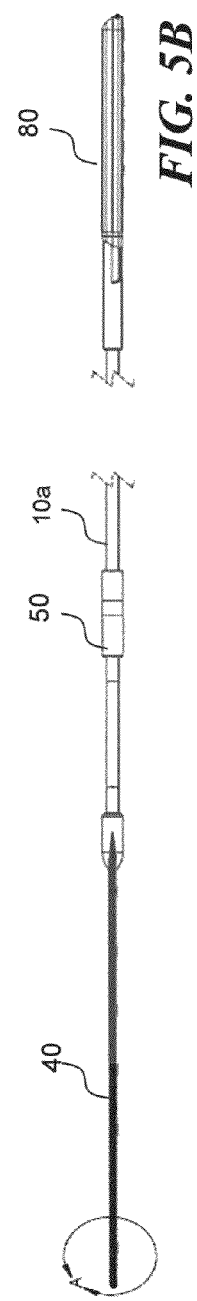
FIG. 5B is a side view of the exemplary implantable medical lead assembly shown in FIG. 5A.
Figure 5C:
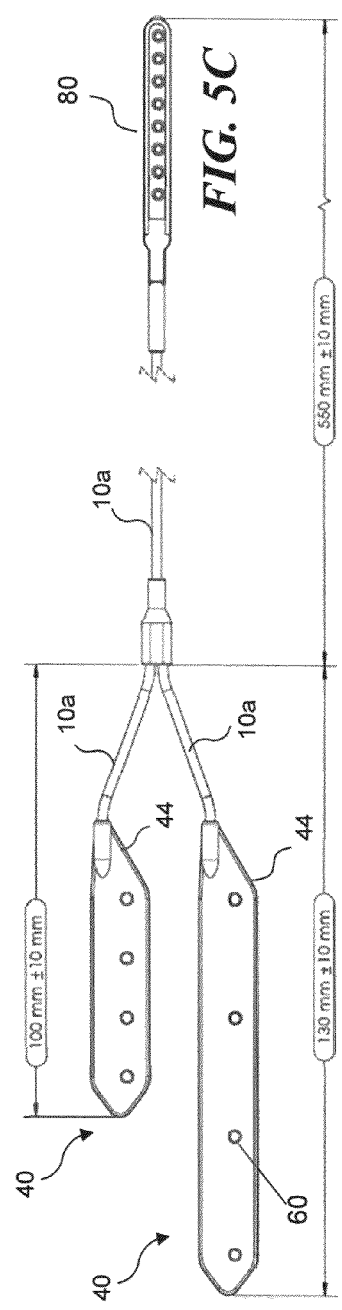
FIG. 5C is the bottom view of the exemplary implantable medical lead assembly shown in FIGS. 5A and 5B.
Figure 5D:
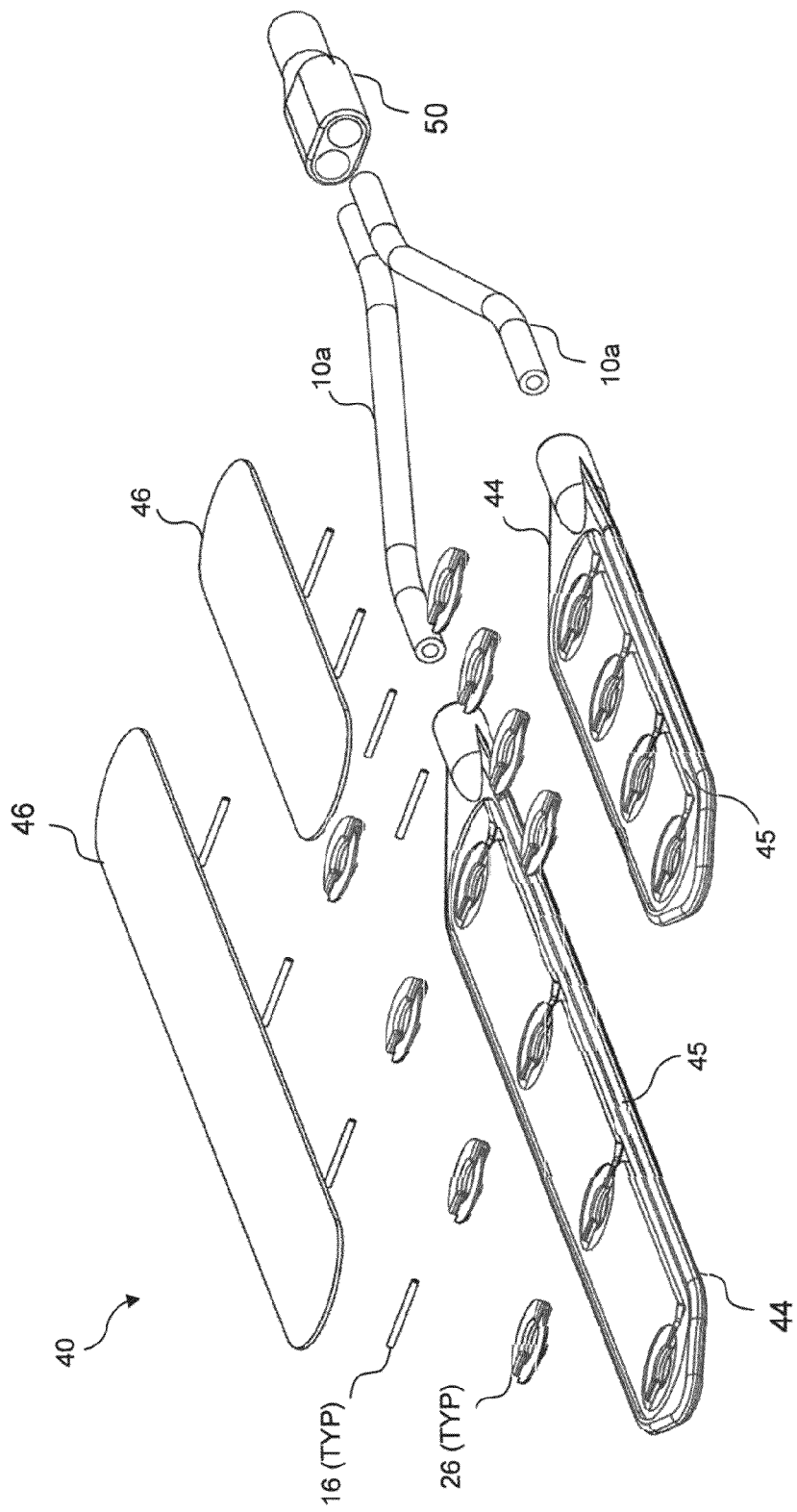
FIG. 5D is an exploded view of the distal strip electrode arrays of the exemplary implantable medical lead assembly of FIGS. 5A-5C utilizing the termination sleeve disclosed herein.

FIGS. 5A, 5B and 5C illustrate the top, side and bottom views of an exemplary implantable medical lead assembly, respectively. FIG. 5D is an exploded view of the implantable medical lead assembly. This exemplary lead assembly is used to monitor electrocorticography (ECoG) signals from the brain and incorporates the termination sleeve disclosed herein. This assembly is intended to be part of a seizure advisory system (SAS) for patients suffering from epilepsy. A more detailed description of systems and algorithms that may use the implantable medical lead assembly are described in commonly owned U.S. Pat. Nos. 6,366,813; 6,819,956; 7,209,787; 7,242,984; 7,277,758; 7,231,254; 7,403,820; 7,324,851; 7,623,928; 7,676,263; 8,036,736; 8,295,934; pending U.S. patent application Ser. No. 11/321,897, filed Dec. 28, 2005; Ser. No. 11/321,898, filed Dec. 28, 2005; Ser. No. 11/322,150, filed Dec. 28, 2005; Ser. No. 11/766,742, filed Jun. 21, 2007, published as U.S. Publ. No. 2007/0150024A1; Ser. No. 11/766,751, filed Jun. 21, 2007, published as U.S. Publ. No. 2008/0027347A1; Ser. No. 11/766,756, filed Jun. 21, 2007, published as U.S. Publ. No. 2008/0021341A1; Ser. No. 12/020,507, filed Jan. 25, 2008, published as U.S. Publ. No. 2008/0183097A1; Ser. No. 12/020,450, filed Jan. 25, 2008, published as U.S. Publ. No. 2008/0183096A1; Ser. No. 12/035,335, filed Feb. 21, 2008, published as U.S. Publ. No. 2008/0208074A1; and Ser. No. 12/180,996, filed Jul. 28, 2008, published as U.S. Publ. No. 2009/0062682A1, the complete disclosures of which are incorporated herein by reference. It should be noted that the termination sleeve concept disclosed herein can be used with other types of implantable medical lead assemblies, and not just the SAS assembly discussed below.

Referring to FIGS. 5A-5D, an SAS including implantable medical lead assemblies has been developed to collect and analyze ECoG signals from the cortical surface of the brain. The ECoG signals are acquired by subdural strip electrode arrays 40 placed over the cortical region of interest. Medical leads are tunneled to a sub-clavicularly disposed implantable telemetry unit (ITU), where a proximal medical lead connector 80 is attached to the ITU. ECoG recordings from the electrodes are transmitted from the ITU to an external patient advisory device (PAD). The PAD will both record and process the ECoG data. Upon algorithmic analysis in near-real time, the PAD will provide indications to the user of whether the probability of a seizure is likely, unlikely or indeterminant. Strip electrode arrays 40 may be implanted below the dura mater via a burr hole or craniotomy. The size of the dura mater penetrations are minimized, while being made large enough to permit proper placement of the electrode arrays.

The implantable medical lead assembly shown in FIGS. 5A, 5B and 5C comprises a lead body 10a (including coiled multifilar wires and a lead body tubing encapsulating all the wires) disposed between proximal connector 80 and a distally disposed strip electrode array 40. Note, it is also possible to have multiple strip electrodes (as shown) within a single implantable medical lead assembly by including a furcation point 50. Each distal strip electrode array 40 is in the form of a substantially flat, flexible paddle that is configured for placement on a cortical surface of the patient's brain, and includes (as additionally illustrated in an exploded view in FIG. 5D) a flexible electrode body 44, a flexible electrode top cover 46 (not shown in FIG. 5A), individual electrode contacts 26 (each of which are welded to wire termination sleeves 16, which are crimped onto the individual wires, as discussed above, and which are disposed in electrode body 44). Note the individual wires servicing each electrode contact 26 are routed along a channel 45 proximate an edge of the electrode body. The electrode body and the electrode top cover are bonded together, to contain the electrode contacts within a semi-flexible distal body at predefined spacing intervals. In this example, the termination sleeves are aligned perpendicular with a longitudinal axis of the distal electrode body.

It should be recognized that the dimensions noted in FIG. 5C are intended to be exemplary, and not limiting. Openings 60 in a bottom surface of flexible electrode body 44 are aligned with electrode contacts 26, enabling such contacts to electrically couple to the cortical region of interest (or some other region of interest).

FIG. 5E illustrates an exploded view of an alternative distal strip electrode array 40a, which directs multifilar wire 32 serving the individual electrode contacts 26 through the center of the electrode contacts via a channel 45a disposed along a central axis of electrode body 44a, as opposed to along an edge of distal strip electrode body 44 as illustrated in FIG. 5D. In this configuration, the termination sleeves are aligned with a longitudinal axis of the distal body. Note that multifilar wire 32 is encapsulated in lead body 10a.

In addition to being used within the distal strip electrode array 40, termination sleeves 16 may also be used within proximal connector 80 of the implantable medical lead assembly (used in connection with an implantable medical device). Each proximal connector 80 serves to electrically couple the medical lead to the implantable medical device. Each proximal connector 80 is disposed at a proximal end of the medical lead and includes a plurality of electrical contacts (employed for coupling to contacts in the implanted medical device). The proximal connector electrical contacts are electrically coupled to a plurality of electrical conductors in the medical lead, which in turn are connected to stimulation and/or monitoring electrodes 26 within each distal strip electrode array 40.

Figure 6A:
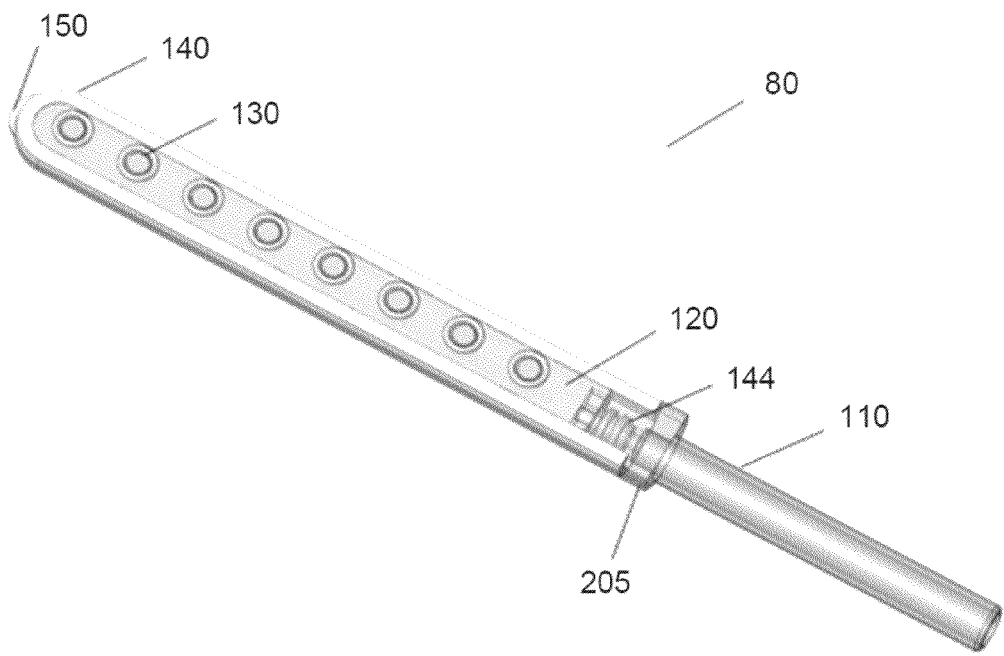
FIG. 6A is a partial cut-away view of a proximal connector electrode assembly.
Figure 6B:
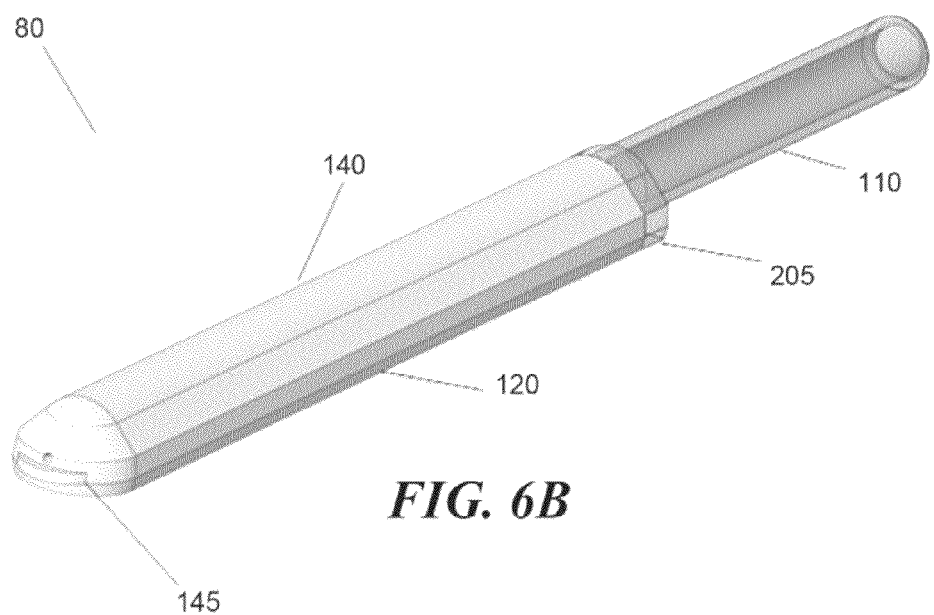
FIG. 6B is a perspective view of the proximal connector electrode assembly of FIG. 6A.
Figure 6C:
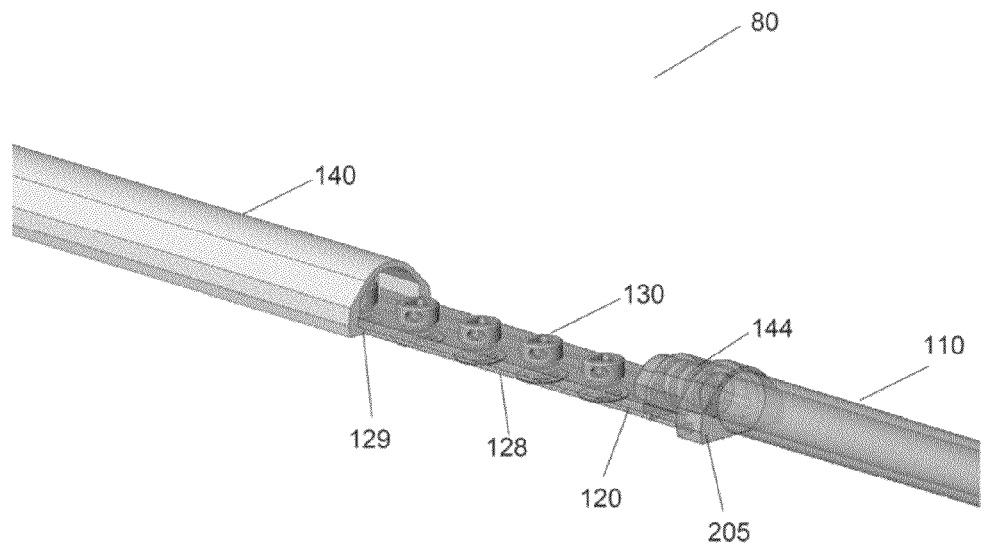
FIG. 6C is a perspective view of the proximal connector electrode assembly of FIG. 6A with the base plate cover partially removed.
Figure 6D:
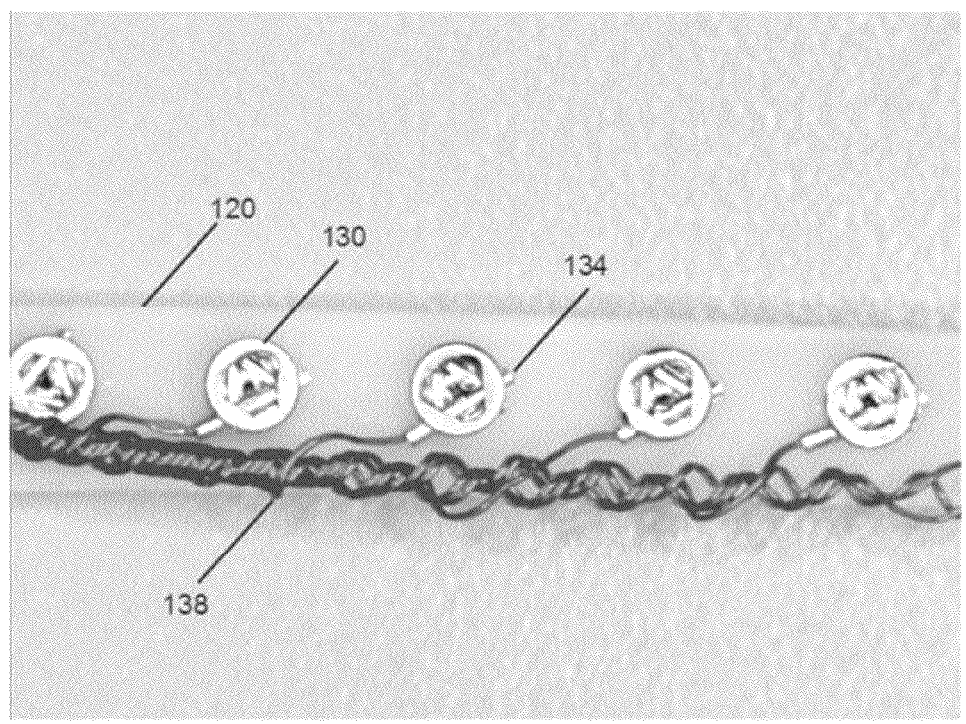
FIG. 6D is a plan view of the top of the base plate of the proximal connector electrode assembly of FIG. 6A.

As shown in FIGS. 6A, 6B, 6C and 6D, an exemplary proximal connector 80 includes a base plate 120, a base plate cover 140, a plurality of electrical contacts 130, and a strain relief sleeve 110. FIGS. 6A and 6B illustrate bottom and top views of proximal connector 80, respectively. FIG. 6C illustrates an exemplary step for an assembly of proximal connector 80, wherein base plate cover 140 is slid over base plate 120 via a tongue and groove feature 129. Proximal connector base plate 120 and base plate cover 140 are made of an insulating material such as plastic, preferably polycarbonate. Electrical contacts 130 are coupled (e.g. pressed in, threaded in or attached by other means) to proximal connector base plate 120. The electrical contacts are preferably made of a highly conductive and biocompatible metal such as Pt/Ir (a platinum iridium alloy). FIG. 6D is a plan view of the top of base plate 120 (without base plate cover 140 in place). Medical lead wires 138 terminate in termination sleeves 134, which are laser welded to electrical contacts 130.

A bottom 128 of base plate 120 (see FIG. 6C) is where electrical contacts 130 are exposed for electrically coupling to the medical implantable device. As noted above, FIG. 6C illustrates proximal connector 80 during assembly, while base plate cover 140 is slid over base plate 120 via a tongue and groove feature 129. Prior to sliding base plate cover 140 over base plate 120, flexible strain relief sleeve 110 is attached to base plate 120. Ribbed structure 144 (part of base plate 120) is where the medical leads (not separately shown in FIG. 6C) are fed through from the exterior of the proximal connector to within the proximal connector so as to terminate at electrical contacts 130. Ribbed structure 144 has outwardly extending molded ribs. Strain relief sleeve 110 (formed of a flexible material such as silicone) has molded interlocking ribs that match the outwardly extending molded ribs of ribbed structure 144, enabling the strain relief sleeve to be attached to base plate 120 via ribbed structure 144. This interlocking ribbed structure enables the silicone strain relief sleeve to remain coupled to the base plate, even if force is applied to the strain relief sleeve or medical lead. As shown in FIG. 6C, when base plate cover 140 is slid over the base plate 120 via tongue and groove feature 129, base plate cover 140 circumferentially surrounds the interlocking ribs. Having the cover surround the interlocking ribs further increases the strength of the strain relief, since base plate cover 140 will prevent the silicone strain relief interlocking portion from deforming and sliding off of the ribbed structure of base plate 120 when under strain. Once base plate cover 140 is slid over base plate 120, the internal volume of proximal connector 80 is backfilled with a filler adhesive (e.g. room temperature vulcanizing silicone). This silicone filler is used to seal the electrodes and connections to be isolated from bodily fluids that are present near the implantation area. The adhesive filler is injected using a backfill hole 150 (FIG. 6A) which is located at one end of base plate cover 140.

As shown in FIGS. 6A-6C, strain relief sleeve 110 includes a compressible shoulder 205, whose function is described below. As shown in FIG. 6B, base plate cover 140 includes a retention ridge 145, whose function is similarly described below.

Figure 7:
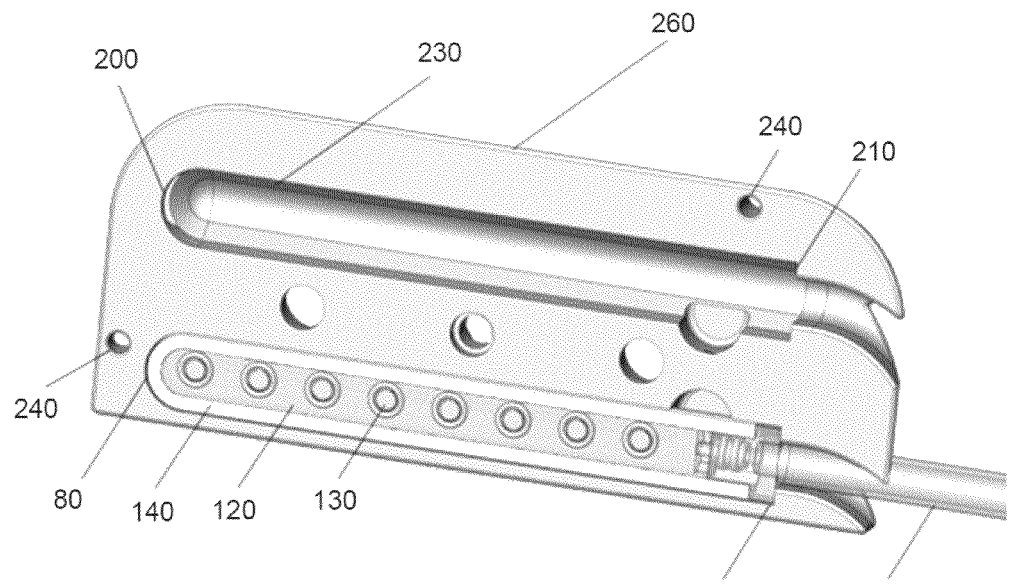
FIG. 7 is a bottom view of the exemplary implantable medical device of FIG. 6A inserted into a top plate configured to hold a plurality of similar devices.
Figure 8:
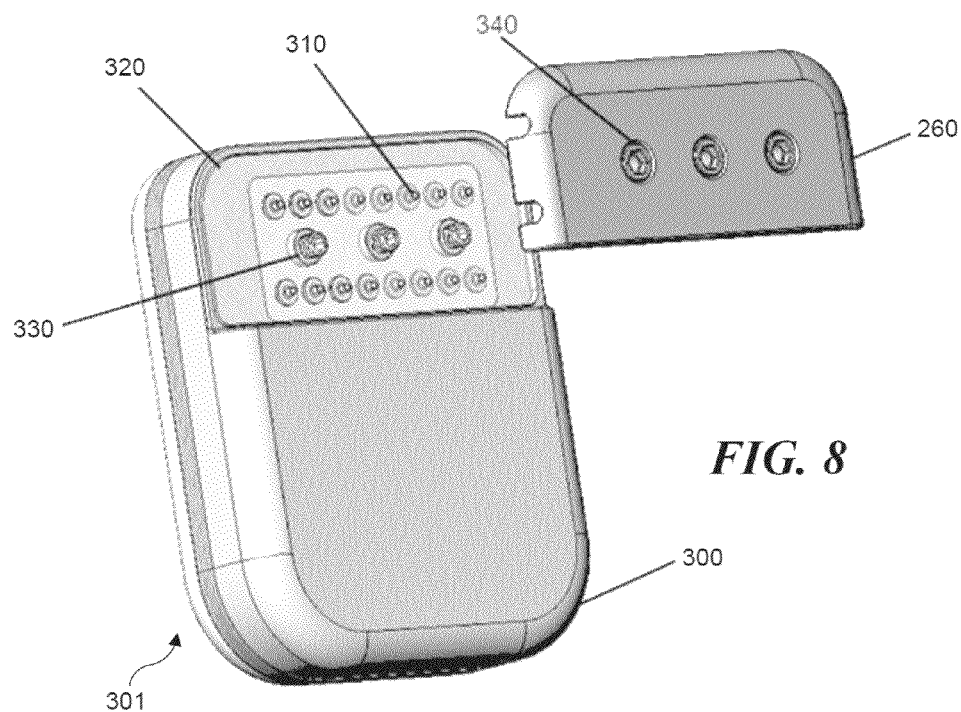
FIG. 8 is a perspective view of an implantable telemetry unit for coupling with the proximal connector of FIGS. 6A-6D.

FIG. 7 illustrates a header cap 260, which serves to receive and align two proximal connectors, and as a means for attaching the header cap to an implantable medical device, as illustrated in FIG. 8. Retention ridge 145 (FIG. 6B) is located at the proximal end of proximal connector 80, and serves to retain the proximal connector within header cap 260, as illustrated in FIG. 7. Header cap 260 includes two recessed channels 230, which serve to receive two proximal connectors 80 (noting that header caps including additional or fewer numbers of such channels can certainly be employed). Each retention ridge 145 (FIG. 6B) engages a receiving indent 200 in header cap 260, the receiving indent acting as a hard stop, which serves to position electrode contacts 130 properly relative to header cap 260, and the implantable medical device electrode contacts (FIG. 8). As noted above, the distal end of the proximal connector includes silicone strain relief sleeve 110, which includes compressible shoulder 205. When placed inside recessed channel 230, compressible shoulder 205 provides for continuous compression, so as to keep the proximal connector retained within recessed channel 230 of header cap 260.

Thus, header cap 260 allows for insertion of proximal connectors 80, automatic alignment of electrode contacts 130, and structure for attaching the proximal connectors to the implantable medical device. FIG. 8 illustrates an implantable medical device 301 including a hermetically sealed housing 300, medical device electrical contacts 310 (which are designed to electrically couple to proximal connector electrical contacts 130), a silicone gasket 320 (which seals header cap 260 against the implantable medical device as well as each of individual electrical contacts 310) and threaded studs 330 (which enable the header cap to be secured to the implantable medical device using capture nuts 340). It should be recognized that the number of studs/capture nuts employed is not critical, and that the three such studs/capture nuts shown in FIG. 8 are exemplary, rather than limiting. In one exemplary embodiment, using a torque setting of 4.5 inch pounds achieves 200 lbs of axial compression on silicone gasket 320. In at least one embodiment, capture nuts 340 on header cap 260 are captured via a washer laser welded onto the header cap, so as to prevent the capture nuts from separating from the header cap, and providing a backstop so that loosening the nut allows the header cap to self-extract from the implantable medical device.

Embodiments of the present invention may provide various advantages not provided by prior art systems. For example, in some embodiments, it is possible to avoid exposing the connection of two different metals to bodily fluids, thereby reducing the risk of galvanic corrosion. In addition, embodiments of the present invention may also provide improved channel isolation by providing improved control over the location and size of conductive elements in the system and reducing any leakage paths. In low voltage systems, such as those used for detecting ECoG or EEG signals, channel isolation may be of extreme importance. Finally, in some embodiments, the use of a rigid and larger diameter termination sleeve can improve handling, thereby increasing ease of manufacturability.

While the invention has been described in terms of particular embodiments and illustrative figures, those of ordinary skill in the art will recognize that the invention is not limited to the embodiments or figures described. For example, in many of the embodiments described above, the medical lead wire is made of a different material than the termination sleeve and electrode. In some applications, this may provide a more desirable combination of material properties. In other embodiments, the lead wire may be made of the same material as the termination sleeve and/or electrode. Depending on the material, it may not be as advantageous to avoid the use of dissimilar metals, but it may still be desirable to use the termination sleeve for improving manufacturability.

In addition, in embodiments described above, the termination sleeve may be coupled with the electrode using laser welding. In other embodiments, the termination sleeve may be electrically coupled with the electrode using other means, such as other forms of welding or structures. For example, the termination sleeve may be provided with a threaded outer surface, which can be received in a threaded female receptacle in or coupled to the electrode.

In yet other embodiments, it may be desirable to integrate the termination sleeve and the electrode into a single component. For example, the electrode may be formed with a deformable cavity into which the lead wire may be received. The cavity may then be coupled to the lead wire using, e.g., laser melting or crimping. This embodiment could reduce the number of components and eliminate the step of fastening the termination sleeve to the electrode.

In addition, in embodiments described above, the termination sleeve and implantable medical lead assembly are used for collecting ECoG signals by implanting the contacts below the dura mater in the brain. In other embodiments, the termination sleeve and contacts may be used in a variety of applications, e.g., intracranial electrodes (e.g., epidural, subdural, and/or depth electrodes), extracranial electrodes (e.g., spike or bone screw electrodes, subcutaneous electrodes, scalp electrodes, dense array electrodes), or a combination thereof.

While it is preferred to monitor signals directly from the brain, it may also be desirable to monitor brain activity using sphenoidal electrodes, foramen ovale electrodes, intravascular electrodes, peripheral nerve electrodes, cranial nerve electrodes, or the like. In a minimally invasive embodiment, the implantable medical lead assemblies may be implanted between the skull and any of the layers of the scalp. Specifically, the electrodes may be positioned between the skin and the connective tissue, between the connective tissue and the epicranial aponeurosis/galea aponeurotica, between the epicranial aponeurosis/galea aponeurotica and the loose aerolar tissue, between the loose aerolar tissue and the pericranium, and/or between the pericranium and the calvarium. To improve signal-to-noise ratio, such subcutaneous electrodes may be rounded to conform to the curvature of the outer surface of the cranium, and may further include a protuberance that is directed inwardly toward the cranium to improve sampling of the brain activity signals. Furthermore, if desired, the electrode may be partially or fully positioned in openings disposed in the skull. Additional details of exemplary minimally invasive implantable devices and their methods of implantation can be found in pending U.S. patent application Ser. No. 11/766,742, filed Jun. 21, 2007, published as Publ. No. 2008/0027515, the disclosure of which is incorporated by reference herein in its entirety. In yet other embodiments, the electrodes may be used for sensing other types of signals elsewhere in the body.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A medical device lead, comprising:
a lead wire having a lead wire end supporting a conductor and a cover; and
a sleeve having an axial sleeve length and an internal hollow portion communicating with a sleeve opening through which the lead wire end extends to dispose the conductor and the cover within the internal hollow portion, the sleeve having a first portion and a second portion each disposed along the axial sleeve length of the sleeve and a third portion disposed between the first portion and the second portion, the third portion defining a third portion sleeve outer dimension about a sleeve axis, the sleeve at the first portion being deformed to sealingly engage the cover and the sleeve at the second portion being deformed to engage the conductor,
wherein at least one of the first portion and the second portion defines a deformed sleeve outer dimension of the sleeve about the sleeve axis, the deformed sleeve outer dimension being less than the third portion sleeve outer dimension.

2. The medical device lead of claim 1, wherein the conductor includes at least one wire, the sleeve at the second portion being mechanically deformed to engage the at least one wire.

3. The medical device lead of claim 1, wherein the conductor includes a plurality of wires, the sleeve at the second portion being mechanically deformed to engage at least one wire of the plurality of wires.

4. The medical device lead of claim 1, wherein the hollow portion defines an inner volume, the deformed sleeve at the first portion providing a seal between the inner volume and the sleeve opening.

5. The medical device lead of claim 1, wherein the conductor comprises a nickel cobalt alloy.

6. The medical device lead of claim 1, wherein the sleeve comprises a platinum iridium alloy.

7. The medical device lead of claim 1, wherein the conductor is a drawn filled tube composite.

8. The medical device lead of claim 1, wherein the conductor is a drawn filled tube (DFT) wire.

9. The medical device lead of claim 1, wherein the deformed sleeve at the first portion is a crimped first portion and the deformed sleeve at the second portion is a crimped second portion.

10. The medical device lead of claim 1, wherein an engagement provided between the lead wire and the sleeve is devoid of welds.

11. The medical device lead of claim 1, wherein a conductive engagement provided within the deformed sleeve at the second portion of the sleeve is contained within a sealed portion of the internal hollow portion.

12. An electrode assembly, comprising:
    an electrode;
    a lead wire having a lead wire end supporting a conductor and a cover; and
    a sleeve coupling the electrode to the lead wire, the sleeve having an axial sleeve length and an internal hollow portion communicating with a sleeve opening through which the lead wire end extends to dispose the conductor and the cover within the internal hollow portion, the sleeve having a first portion and a second portion each disposed along the axial sleeve length of the sleeve and a third portion disposed between the first portion and the second portion, the third portion defining a third portion sleeve outer dimension about the sleeve axis, the sleeve at the first portion being deformed to sealingly engage the cover and the sleeve at the second portion being deformed to engage the conductor,
    wherein at least one of the first portion and the second portion defines a deformed sleeve outer dimension of the sleeve about the sleeve axis, the deformed sleeve outer dimension being less than the third portion sleeve outer dimension.

13. The electrode assembly of claim 12, wherein the conductor is a drawn filled tube composite.

14. The electrode assembly of claim 12, wherein the conductor is a drawn filled tube (DFT) wire.

15. The electrode assembly of claim 12, wherein the deformed sleeve at the first portion is a crimped first portion and the deformed sleeve at the second portion is a crimped second portion.

16. The electrode assembly of claim 12, wherein the electrode and the sleeve comprise a same material.

17. The electrode assembly of claim 13, wherein an engagement provided between the lead wire and the sleeve is devoid of welds.

18. The electrode assembly of claim 13, wherein a conductive engagement provided within the deformed sleeve at the second portion of the sleeve is contained within a sealed portion of the internal hollow portion.

19. A medical device lead comprising:
    a lead wire having a lead end supporting a conductor and a cover, the cover defining a cover outer diameter and the conductor defining a conductor outer diameter, the cover outer diameter being greater than the conductor outer diameter; and
    a sleeve having an axial sleeve length and an internal hollow portion communicating with a sleeve opening through which the lead wire end extends to dispose the conductor and the cover within the internal hollow portion, the sleeve having a first portion and a second portion each disposed along the axial sleeve length of the sleeve with the first portion aligned with the cover and the second portion aligned with the conductor,
    wherein the internal hollow portion has a pre-deformation state and a post-deformation state such that the internal hollow portion in the pre-deformation state has a uniform pre-deformation inner diameter extending along the axial sleeve length from the first portion to the second portion and the internal hollow portion in the post-deformation state has a plurality of post-deformation inner diameters extending along the axial sleeve length from the first portion to the second portion, and
    wherein at least a portion of the sleeve in the post-deformation state is in contact with the conductor.

20. The medical device lead of claim 19, wherein the conductor comprises at least one of a nickel cobalt alloy, a drawn filled tube composite, and a drawn filled tube (DFT) wire.

21. The medical device lead of claim 19, wherein the sleeve comprises a platinum iridium alloy.

* * * * *